(12) United States Patent
Skulachev

(10) Patent No.: US 9,328,130 B2
(45) Date of Patent: *May 3, 2016

(54) METHOD OF TREATING ORGANISM BY BIOLOGICALLY ACTIVE COMPOUNDS SPECIFICALLY DELIVERED INTO MITOCHONDRIA, PHARMACEUTICAL COMPOSITION REQUIRED FOR THE USE OF THE METHOD AND A COMPOUND APPLICABLE FOR THIS PURPOSE

(75) Inventor: Vladimir Petrovich Skulachev, Moscow (RU)

(73) Assignee: MITOTECH S.A., Luxembourg (LU)

(*) Notice: Subject to any disclaimer, the term of this patent is extended or adjusted under 35 U.S.C. 154(b) by 0 days.

This patent is subject to a terminal disclaimer.

(21) Appl. No.: 11/972,437

(22) Filed: Jan. 10, 2008

(65) Prior Publication Data

US 2008/0176929 A1   Jul. 24, 2008

Related U.S. Application Data

(63) Continuation of application No. PCT/RU2006/000394, filed on Jul. 24, 2006.

(30) Foreign Application Priority Data

Oct. 18, 2005 (RU) .............................. 2005132217

(51) Int. Cl.
```
A01N 57/00     (2006.01)
A61K 31/66     (2006.01)
C07D 311/82    (2006.01)
C07F 9/54      (2006.01)
A61K 47/48     (2006.01)
```

(52) U.S. Cl.
CPC .......... *C07F 9/5442* (2013.01); *A61K 47/48023* (2013.01); *A61K 47/48061* (2013.01); *C07F 9/5456* (2013.01)

(58) Field of Classification Search
USPC .......................................... 514/125; 549/388
See application file for complete search history.

(56) References Cited

U.S. PATENT DOCUMENTS 6,331,532 B1* 12/2001 Murphy et al. ............... 514/100

OTHER PUBLICATIONS

Dorwald F. A. (Side reactions in organic synthesis, 2005, Wiley, VCH, Weinheim, p. IX of Preface).*
Coulter et. al. (Free Radical Biology and Medicine (2000) 28:1547-1554).*
Kelso et. al. (The Journal of Biological Chemistry (2001) 276:4588-4596).*
Wanke et. al. (Plant Science (2000) 154:183-187).*
Kruk et. al. (Chemistry and Physics of Lipids (1997)87:73-80).*
Liu et. al. (Photosynthesis Research (1991) 30:95-106).*

* cited by examiner

*Primary Examiner* — Marcos Sznaidman
(74) *Attorney, Agent, or Firm* — Wayne A. Keown; Verrill Dana LLP

(57) ABSTRACT

This invention relates to biology and medicine and, in particular, can be used in medicine to make a pharmaceutical composition for targeted delivery of biologically active substances into mitochondria, driven by proton electro-chemical potential in the mitochondria. This invention also relates to the method to affect an organism by the targeted delivery of biologically active compounds to mitochondria. The invention can be useful in treatment of diseases or disorders associated with not normal functioning of mitochondria, in particular diseases associated with increased production of free radicals and reactive oxygen species.

1 Claim, 9 Drawing Sheets

A

B

METHOD OF TREATING ORGANISM BY BIOLOGICALLY ACTIVE COMPOUNDS SPECIFICALLY DELIVERED INTO MITOCHONDRIA, PHARMACEUTICAL COMPOSITION REQUIRED FOR THE USE OF THE METHOD AND A COMPOUND APPLICABLE FOR THIS PURPOSE

FIELD OF THE INVENTION

This invention relates to biology and medicine and, as an example of its application, provides a method of preparation of pharmaceutical compositions for targeted delivery of biologically active molecules into mitochondria, driven by proton electro-chemical potential. The invention also provides a method to treat an organism by said compounds delivered into mitochondria.

BACKGROUND OF THE INVENTION

Mitochondria play key roles in many vital processes of a living cell. The list of such processes includes energy conversion (since the principle function of mitochondria is to provide the cell with energy), metabolism of certain substances (e.g. fatty acids), etc. Mitochondria are also directly involved in production and utilization of free radicals (FR) and reactive oxygen species (ROS)—extremely active compounds that can affect many processes within a living cell. Finally, mitochondria have been recently proved to play a key role in the process of programmed cell death.

Many diseases are known to be related to the dysfunction of mitochondria. This includes all disorders connected to increased production of FR and ROS, single or mass dying of cells within a tissue of an organ, dysfunction of programmed cell death mechanism (apoptosis), dysfunction of fatty acid metabolism etc.

It is assumed that by affecting mitochondria different aspects of functioning of the whole organism can be improved.

Within the framework of the invention a new method is developed to affect mitochondria within a living cell via targeted delivery and accumulation of biologically active compounds inside these organelles.

This approach possesses some obvious advantages. Targeted delivery of a compound allows to increase the efficiency of its application, to reduce the dosage (since the effective dose of the compound is achieved only inside the target compartment of the cell), to reduce probability and strength of side-effects.

The functional organization of mitochondria itself provides a unique opportunity for the targeting—functioning mitochondrion actively pumps-out protons from its matrix into cytoplasm. This process creates an extremely high electro-chemical potential of hydrogen ions (proton potential) on the inner membrane of mitochondrion.

Bioenergetic studies have resulted in finding of a number of compounds that can penetrate mitochondrial membrane and actively accumulate inside mitochondria in a proton potential-dependent fashion. These compounds were called "Skulachev-ions" (Green D. E., "The electromechanochemical model for energy coupling in mitochondria", 1974, Biochem. Biophys. Acta., 346:27-780). Such ions usually do not reveal any significant biological activity. The main idea of the invention is to use "Skulachev-ions" to create new compounds that includes besides a "Skulachev-ion" some residue (in terms of the invention—effector moiety, or effector) which should be delivered into mitochondria.

At the moment a very limited number of mitochondrially-targeted biologically active compounds is known. Some related compounds are described in inventions U.S. Pat. No. 6,331,532 and EP 1047701 (mitochinol (MitoQ), Mitovitamin E (MitoVitE)) and EP 1534720 (superoxide dismutase and glutathione peroxidase mimetics, linked to an alkyl triphenilphosphonium). Some of these compounds are described in papers discussed below.

Compounds carrying superoxide dismutase and glutathione peroxidase mimetics are claimed in EP1534720 as mitochondrially targeted antioxidants suitable for treatment of diseases related to oxidative stress. In experimental examples that illustrate the invention EP1534720 it is shown that these compounds can penetrate mitochondrial membrane and accumulate inside mitochondria. Antioxidant abilities of the compounds were shown by studying of non-biological reactions (as chemical properties of substances or when interacting with isolated mitochondria in vitro). No data are presented on the effect of these mimetics upon the living cell and organism. Such mimetic compounds are most likely to interact with SH-groups of proteins. This can dramatically reduce efficiency and seriously limit possible application of mitochondrially-targeted antioxidants carrying mimetics of superoxide dismutase as well as glutathione peroxidase (so called ebselen), as has been shown by Filipovska A, Kelso G F, Brown S E, Beer S M, Smith R A, Murphy M P. J. Biol. Chem. 2005, 280(25):24113-26. This study has demonstrated that ebselen covalently linked to a mitochondria-targeting moiety (Mitoebselen) is of the same antioxidant efficiency as normal nontargeted ebselen. Therefore, even if mitoebselen is more active antioxidant comparing to ebselen, this positive property of mitoebselen is diminished by its undesired side activity.

Another substance claimed as mitochondrially targeted antioxidant is MitoVitE i.e. a compound containing triphenylphosphonium as targeting moiety and vitamin E as an antioxidant. Description of the invention EP 1047701 discloses data showing some antioxidant activity of this compound shown in rat brain homogenate as well as an ability of MitoVitE to penetrate isolated mitochondria and living cells in culture. It has been shown that 10 µM MitoVitE has no toxic effect on cells in culture. However, higher concentrations resulted in cell death. It should be noted that no antioxidant activity of MitoVitE on cells in culture, tissue or entire organism has been demonstrated.

The effect of MitoVitE on cell culture is described in publication Jauslin M L, Meier T, Smith R A, Murphy M P, FASEB J. 2003 17(13):1972-4. It was found that MitoVitE is able to prevent apoptosis in cultured cells; however, this effect is retained even in the presence of an uncoupler FCCP (3-fluoromethyl-carbonylcionide phenylhydrazone) that switches off targeted accumulation of MitoVitE in mitochondria. These data show that even if MitoVitE is targeted to mitochondria, such targeting does not play a significant role in its biological effect.

Mitochondrially targeted antioxidant MitoQ and its variants (MitoQ5, MitoQ3) consist of ubiqinon (ubiqinol in its reduced form) linked to triphenylphosphonium by C-10 linker (C5, C3 accordingly). In the description of invention U.S. Pat. No. 6,331,532, MitoQ is claimed as active compound for pharmaceutical compositions suitable for treatment or prophylactics of disorders related to oxidative stress. Experimental examples of this invention demonstrate antioxidant properties of MitoQ in cell-free systems, its ability to penetrate isolated mitochondria in vitro, effect of this compound on respiration of isolated mitochondria in vitro. However no data on the effect of MitoQ on living cells, tissue, organs of entire organism are presented in U.S. Pat. No. 6,331,532.

Some additional data can be found in PCT WO2005019233 of the same group of inventors, where they show that MitoQ is able to prevent lipid peroxidation of isolated mitochondria in vitro. Some other data are published in Adlam V J, Harrison J C, Porteous C M, James A M, Smith R A, Murphy M P, Sammut I A, 2005, FASEB J. 19:1088-95.

In this study the authors have presented the only so far known example of MitoQ action on living organism in the experiment of feeding rats with MitoQ, followed by the study of their heart function with the Langendorff method (isolated heart perfusion). The data obtained indirectly support the claim that MitoQ can be used for prophylaxis or therapy of myocardial ischemic damage. However, several inaccuracies and arguable points of this study do not allow to consider this claim proved. In fact, the model used by the authors—30-minute normothermic ischaemia followed by reperfusion is a standard method to study ischaemic damage of myocardium. However, the major disadvantage of this method is the electric instability of the isolated heart during reperfusion. It is well known that a certain number of hearts cannot restore their activity due to periodical or constant fibrillation, and periodical arrhythmia is to occur in almost every heart during the experiment. Surprisingly, there is indication of neither fibrillation nor arrhythmia in this article. Therefore it remains uncertain, whether the results obtained characterize average properties of the whole group of experiments or only those experiments in which the arrhythmia was less pronounced. Besides, taking into account the above reasons, it is clear that the number of animals in each experimental group (six) is not sufficient for such a complicated experimental model.

The statement that the results presented in this work are not completely correct is partially supported by a rather strange observation of a significant increase in the contractile function in both control and experimental groups during reperfusion that should be followed by inevitable death of some cardiomyocytes. This result could be obtained if the calculation of the contractile function was performed using only active hearts, excluding "switched off" unstable ones, while, the rate of perfusion was calculated using all hearts. Such method is obviously incorrect. Whereas average results in MitoQ treated hearts are higher than control ones, these groups have not been compared directly and thus the significance of this difference is not clear.

Thus, the claim that MitoQ is a cardioprotector compound seems to be not convincing. Unfortunately there are no control group data on mitochondrial ultrastructure, lactate dehydrogenase loss from the heart, as well as measurements of cytochrome c release from mitochondria as well as caspase 3, complex I and aconitase activity.

In conclusion, accurate analysis of this study reveals some vulnerable points especially at stages of selection and analysis of obtained results. Most likely the authors are not very experienced with the model used. Therefore the cardioprotective action of MitoQ remains unproved.

It should also be noted that despite some promising observations concerning the MitoQ action, there are several results and calculations that cast doubt on the possibility of practical application of this compound. For example, it was shown in experiments with cell culture that MitoQ provides its antioxidant and anti-apoptotic action at concentration about 1 μM in the medium. It means that MitoQ concentrations inside the mitochondria should be 1 mM provided that membrane potential is about 180 mV. On the other hand, it was shown by Smith R A, Porteous C M, Gane A M, Murphy M P, *Proc Natl Acad Sci USA,* 2003, 100(9):5407-12 when feeding MitoQ to animals, the accumulation of MitoQ in the most oxidative stress sensitive tissues (heart and brain) amounts up to 100 pmoles/gram, which corresponds to the MitoQ concentration inside heart mitochondria equal to 100 nM. This is more than 1000 times lower than the concentration shown to be efficient in the cell culture experiments. Formally, the concentration can be raised by the increase of amounts of MitoQ fed to animals, but this is, in fact, not possible due to the toxicity of the compound.

Summarizing the data above, all the mitochondrially targeted compounds disclosed so far are mitochondrially targeted antioxidants. No other mitochondrially-targeted biologically-active compounds are known to date. It should be remarked that the described substances claimed as mitochondrially targeted antioxidants cannot be applied yet to the claimed purposes and their perspectives are unclear due to the lack of information on their biological activity, especially taking into account that most of them have already been proved inefficient or toxic.

DESCRIPTION OF THE INVENTION

The invention is based on the principle that a biologically-active compounds, being linked with a Skulachev-ion, can be specifically delivered to mitochondria at the expense of energy of electrochemical potential of hydrogen ions. Such an approach has allowed to multifold decrease the amount of biologically active substances administered and to specifically affect mitochondria, that are the key element in the most important intracellular processes. Thus the elaborated approach allows to dramatically decrease unfavorable side effects of the biologically-active compound employed.

Thus, one of the aspects of the given invention is the way to affect an organism by biologically active substances targetedly delivered to mitochondria at the expense of energy of electrochemical potential of hydrogen ions.

The further aspect of the invention is the composition for targeted delivery of biologically active substance comprising a compound that includes (a) the targeting moiety providing delivery of the entire compound inside mitochondria, (b) the linker group and (c) the effector—a substance with the required biological activity. In general, such a compound can be described by the following structure:

(structure I)

wherein A—effector of structure:
a) antioxidant

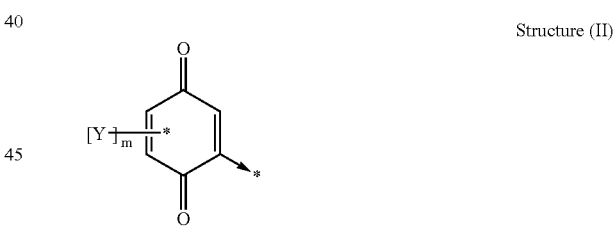

Structure (II)

and/or reduced form thereof
wherein m is an integer from 1 to 3; each Y is independently selected from the group consisting of: lower alkyl, lower alkoxy; or two adjacent Y groups, together with carbon atoms to which they are attached to form the following structure:

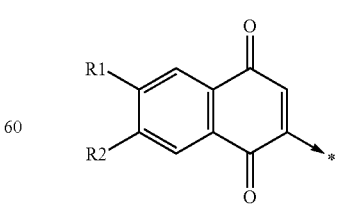

and/or reduced form thereof
wherein R1 and R2 may be the same or different and are each independently lower alkyl or lower alkoxy;

with proviso that the antioxidant is able to react with enzymes of mitochondria respiratory chain in order to neutralize its radical form created by interaction with free radicals and reactive oxygen species, and to restore its original (fully reduced) form. It is preferable that the difference between minimal concentration having antioxidant action and minimal concentration having prooxidant action on mitochondria would be at least 10 fold;

b) pro-oxidant;
c) apoptosis inductor or inhibitor of anti-apoptosis proteins of mitochondrial localization;
d) photosensitizer;

In the broadest aspect of the present invention:

Antioxidant is a compound which can neutralize reactive oxygen species. In a preferred embodiment, said antioxidant in its radical (half-reduced) form, appeared as a result of reduction of ROS, is able to be converted by mitochondrial respiratory chain back to the initial fully reduced form.

Preferred antioxidant of the structure (II) of the present invention is 2,3-dimethyl-1,4-benzoquinol (plastoquinol—an extremely powerful antioxidant from the most $O_2$-rich compartment of the living cells i.e. thylakoids of plant chloroplasts);

Prooxidant is a compound which can form and/or induce formation of free radicals and reactive oxygen species when having been delivered into a cell. Preferable prooxidants of the present invention are: paraquat, menadione or organic hydroperoxides;

Apoptosis inductor is a compound which induces programmed cell death (apoptosis) when delivered in mitochondria of a living cell. Preferable apoptosis inductor of the present invention is phenylarsenicoxide, an effective apoptosis inductor that stimulates formation of mitochondrial pore;

Inhibitor of anti-apoptosis proteins of mitochondrial localization is a compound which is able to interact with one or more of anti-apoptosis proteins localized in mitochondria (including membrane anti-apoptosis proteins) and suppress their activity. Preferable inhibitor of anti-apoptosis proteins of mitochondrial localization of the present invention is ABT737. The proposed compound is assumed to be especially efficient apoptosis inducer when combined with some chemotherapeutical agent;

Photosensitizer is a compound which is able to produce singlet oxygen or other reactive oxygen species or free radicals under illumination. Preferred photosensitizers of the present invention are: phthalocyanine optionally containing metal or metal complexes; porphyrin and its derivatives, particularly BDP-Ma$_C$ or BDP-Ma$_D$; or foscan (mTHPC).

L—linker group, comprising:
a) straight or branched hydrocarbon chain optionally substituted with one or more substituents and optionally containing one or more double or triple bonds;
b) natural isoprene chain;
n is integer from 1 to 20;
B—comprising:
a) Skulachev-ion Sk:

Sk⁺ Z⁻ where Sk is a lipophilic cation, Z is a pharmacologically acceptable anion;
b) charged hydrophobic peptide containing 1-20 amino acid residues;
with proviso that in compound of structure (I) A is neither ubiquinone (e.g. 2-methyl-4,5-dimethoxy-3,6-dioxo-1,4-cyclohexadienyl) nor tocopherol or mimetic of superoxide dismutase or ebselen; with L—neither divalent decyl nor divalent pentyl or divelnt propyl radical; and with B is triphenylphosphonium cation;
including solvates, isomers, prodrugs and pharmaceutically acceptable carrier thereof.

The further aspect of the invention includes a therapeutic or prophylactics agent—a compound of structure (I)—effective in treating of diseases which can be cured or prevented by lowering the amount of free radicals or reactive oxygen species in living cells, tissues, sites, organs or in the entire organism with the help of mitochondrially targeted antioxidants. This aspect of the invention includes the following:

use of mitochondrially targeted antioxidants of structure (I) to prolong a life span of humans or animals;

use of therapeutic or prophylactic agent effective when a disease is caused by aging of organism and by increase of oxidative stress;

in particular use of mitochondrially targeted antioxidants to treat ophthalmologic diseases caused by oxidative stress and/or massive death of retinal cells, involved in processes providing vision; to treat cataract; to treat retina macular degeneration;

use of mitochondrially targeted antioxidants of structure (I) for treatment or prophylactics of diseases caused by mass programmed cell death in tissues and organs and/or associated with spread of signals initiating programmed cell death through the damaged tissue;

use of mitochondrially targeted antioxidants of structure (I) for treatment and/or prophylactics of cardio-vascular diseases, when programmed cell death, apoptosis or necrosis play a key role; for treatment and/or prophylactics of heart attack, stroke; to prevent harmful effects of reoxygenation or ishaemic damage of different organs.

use of mitochondrially targeted antioxidants of structure (I) during surgical intervention to protect healthy tissues from damage;

use of mitochondrially targeted antioxidants of structure (I) during transplatation to prevent rejection of transplanted material as well as for protection of said material before transplantation;

use of mitochondrially targeted antioxidants of structure (I) in cosmetology, to overcome consequences of burns, to stimulate healing of wounds, including surgical stitches or sutures.

use of mitochondrially targeted antioxidants of structure (I) as an antiinflammatory compound.

In a further aspect, the invention provides an agent—compound of structure (I)—for treatment or prophylaxis of cancer diseases. This aspect comprises:

use of mitochondrially targeted anticancer agents to prevent formation of metastases, angiogenesis, as well as for targeted initiation of programmed cell death of cancer cells.

use of mitochondrially targeted prooxidants of structure (I) as mitochondrially targeted anticancer agents, preferable mitochondrially targeted prooxidants are mitochondrially targeted paraquat, mitochondrially targeted menadion, or mitochondrially targeted antioxidants incapable in being restored (reduced) by the mitochondrial respiratory chain and, thus, manifesting prooxidant properties (for example compound DMMQ described in examplification);

use of mitochondrially targeted inducers of apoptosis of structure (I) as mitochondrially targeted anticancer agent. Such an approach is preferable in comparison with traditional inducers of apoptosis, as mitochondria provide a great amount of possibilities to trigger programmed cell death. One of the best ways of such an initiation is chemical linkage of SH groups of mitochondrial membrane proteins with the help of effector group of mitochondrially targeted inducer of apoptosis of structure (I). The preferable effector group of such a compound is phenylarsenicoxide;

use of mitochondrially targeted inhibitors of antiapoptotic proteins of mitochondrial localization as mitochondrially targeted anticancer drugs of structure (I). Preferable proteins, the activity of which should be inhibited by such compounds, are bcl-2 and related proteins. One of the most preferable inhibitors is ABT737.

In a further aspect, the invention provides an application of, as mitochondrially targeted anticancer drug, a composition comprising mitochondrially targeted inhibitors of antiapoptotic proteins of mitochondrial localization and traditional drugs inducing programmed cell death of cancer cells.

In a still further aspect, the invention provides
use of a composition comprising (i) a mitochondrially targeted antioxidant of structure (I) and (ii) standard medicaments that induce programmed cell death of cancer cells. In this aspect of the invention, application of antioxidants linked to lipophylic cations is preferable, as in cancer cells activity of enzymes capable of pumping out lipophylic cations (enzymes responsible for multiple drug resistance) is shown to be strongly increased. Thus, mitochondrially targeted antioxidant will be mostly accumulated in healthy cells that will result into their preferable survival during anticancer therapy, which in turn will lower the amount of undesirable side-effects of said therapy;
use of mitochondrially targeted antioxidants to increase efficiency of chemio- or radiotherapy of cancer;
use of mitochondrially targeted photosensitizer as a mitochondrially targeted anticancer drug;
use of mitochondrially targeted photosensitizer in photodynamic therapy of cancer that allows mitochondrial induction of apoptosis. This approach is preferable comparing to standard photodynamic therapy as it (i) allows to eliminate cancer cells with the help of programmed cell death and not necrosis (associated with a number of undesired consequences), (ii) allows to decrease the amount of photosensitiser administered that also reduces undesired side-effects.
use of mitochondrially targeted antioxidant SkQ1 as preferable anticancer agent.

The further aspect of the invention is a method of disinfection of tissues, blood or other cells containing substances with the help of free radicals. Within this aspect desired cells and cell elements are protected by mitochondrially targeted antioxidant, while all undesired microorganisms are killed by free radicals.

In a still further aspect, the invention provides application of mitochondrially targeted antioxidants for increasing of viability of human or animal cells in cell culture for research or technology needs. This aspect of the invention is based on the fact of usually increased concentration of oxygen in cell culture medium comparing to normal tissue, that increases a probability of oxidative stress of cells, which in its turn leads to higher probability of apoptosis and necrosis, decreasing the viability of the cells. Administration of mitochondrially targeted antioxidants dramatically reduces oxidative stress. Treatment of cells with mitochondrially targeted antioxidants also significantly increases the biomass of the cells, and thus rises their productivity. This aspect of the invention provides:
use of mitochondrially targeted antioxidants to increase productivity of human, animal, plant or fungi cells in cell culture producing pharmaceuticals.
use of mitochondrially targeted antioxidants to increase productivity of whole plants when used for production of pharmaceuticals: proteins (including antibodies);
use of mitochondrially targeted antioxidants to increase productivity of yeasts or other fungi of genera *Saccharomyces, Pichia, Hansenula, Endomyces, Yarrowia* in cell culture when used for production of pharmaceuticals: proteins, antibodies;
use of mitochondrially targeted antioxidants to increase viability of plant protoplasts in cell culture, when used for production of pharmaceuticals; proteins; antibodies, as well as for generation of genetically modified plants;
use of mitochondrially targeted antioxidants in generation of transgenic plants to increase viability of regeneration of plants, cells in cali;
use of mitochondrially targeted prooxidants to repel pathogenic microorganisms—protozoa, fungi, bacteria.

In a further aspect the invention provides a method of synthesis of mitochondrially targeted antioxidants with lipophilic cation as the targeting moiety.

Figure 1:
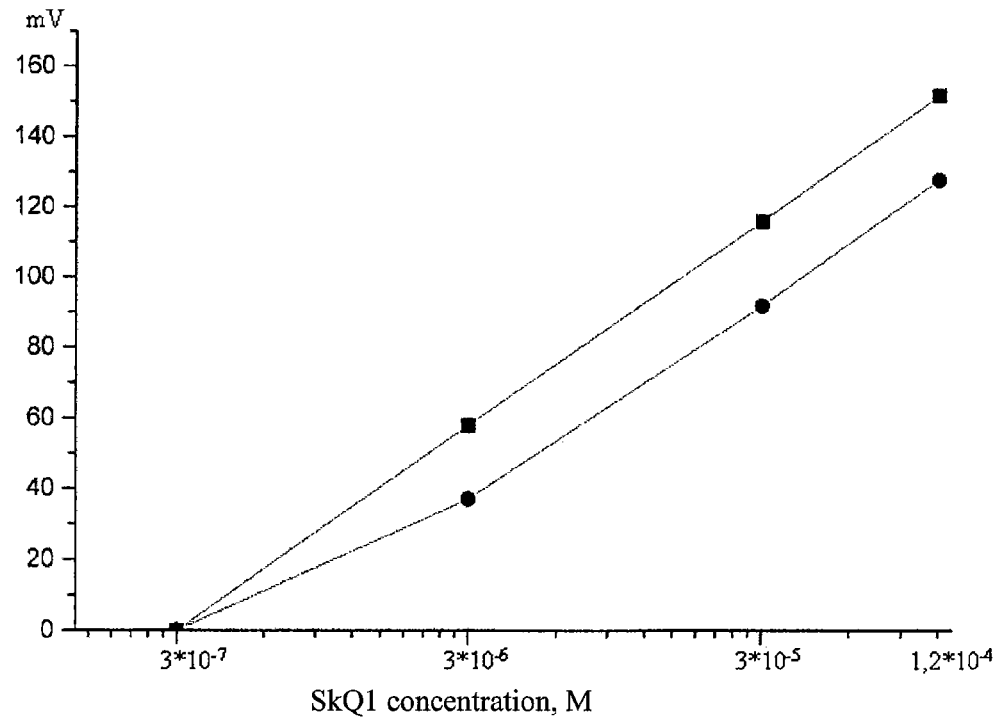
FIG. 1 shows the transfer of SkQ1 across the planar bilayer phospholipid membrane.

The following non-limiting Examples illustrate the preparation and use of the compounds of structure I but should not be understood as limiting the invention as modifications in materials and methods will be apparent to the skilled person. The following examples should not be construed as limiting the scope of this disclosure.

EXAMPLES

Experimental Example I

Synthesis of Compounds of Structure (I)

Synthesis of SkQR1 (rhodamine G 2,3-dimethyl-1,4-benzoquinon-5-decyl ester)

Compound SkQR1—Compound of Structure (I) (Wherein A—Fragment of Plastoquinone—Natural Antioxidant from Chloroplast Thylakoid, B—Rhodamine G)

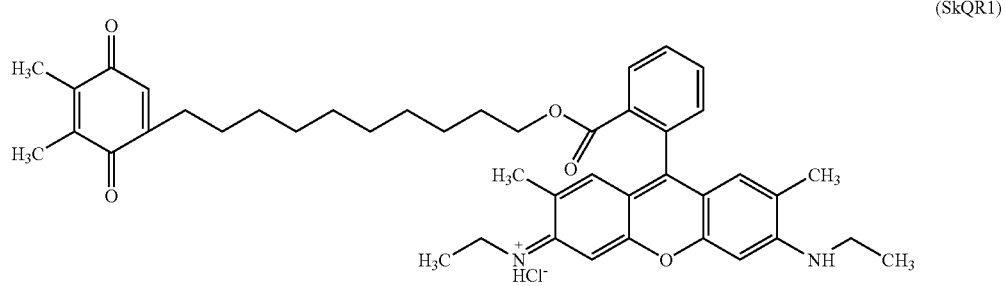

(SkQR1)

Materials and methods: 2,3-Dimethyl-hydroquinone, 11-bromoundecanoic acid, rhodamine G, N,N'-dicyclohexylcarbodiimide, potassium bromate, silver nitrate, ammonium persulfate, cesium carbonate were purchased from Fluka, Aldrich, Sigma or Merck; Column chromatography was carried out on silica gel "Silicagel 60" (0.063-0.2 mm), Merck; Solvents: DMF, dichloromethane, benzene, chloroform, ethyl acetate, acetone, acetonitrile, THF, hexane, absolute ethanol, iso-propanol and methanol were used as received.

TLC was carried out on silica gel TLC plates "Kieselgel 60 $F_{254}$" (Merck). Compounds were visualised under short wave UV and stained by ammonia vapours for quinone-containing species.

UV-spectra were recorded on a <<Cary 50 Bio>> spectrometer (Varian).

HPLC analysis and purification were carried out on Adjilent 1100 with gradient of acetonitrile in 10 mM $H_3PO_4$.

MALDI-TOF or ESI mass spectra were run on a Ultraflex or Autoflex (Bruker Daltonik, Germany), with 337 nm laser.

Infrared spectra were recorded in film on Specord 40.

$^1$H- and $^{13}$C-NMR spectra were measured at 303K using a Bruker Avance-400 spectrometer Synthesis of SkQR1 is illustrated at Scheme 1.

Scheme 1

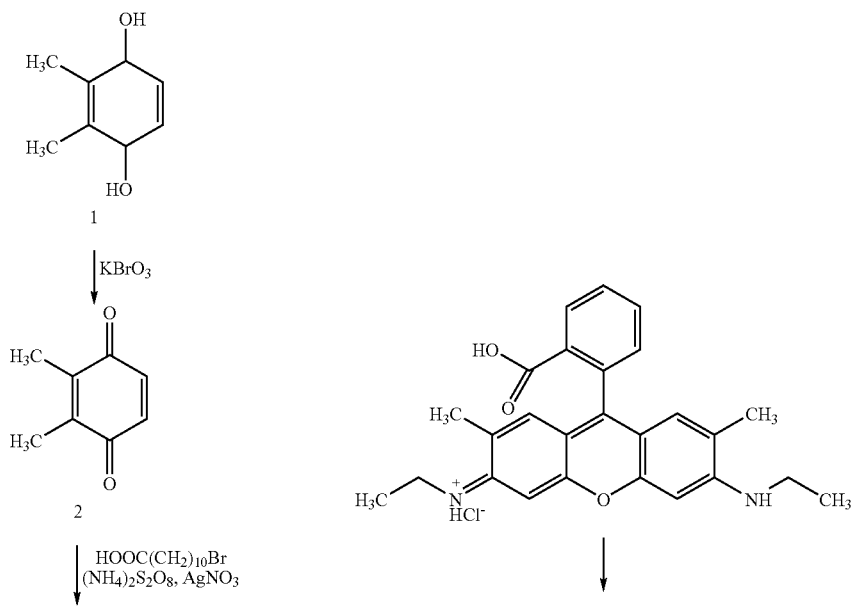

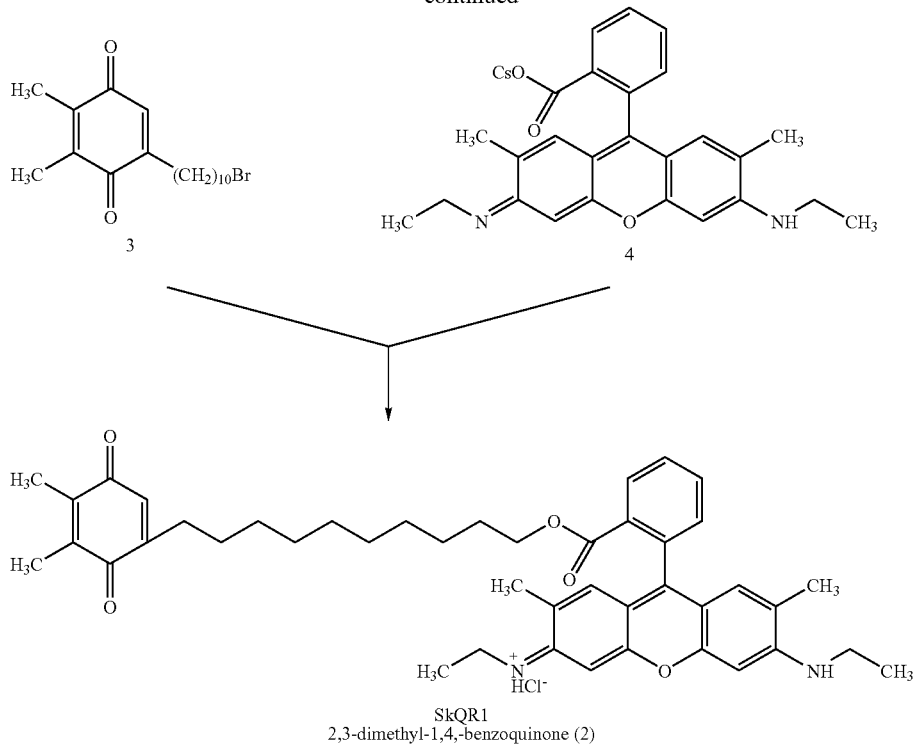

SkQR1
2,3-dimethyl-1,4,-benzoquinone (2)

0.83 g (6 mmol) of 2,3-dimethylhydroquinone was added to the solution of 0.34 g (2 mmol) potassium bromate in H2O (6 ml) and 5N sulfuric acid (0.3 ml). The mixture was heated to 60° C. and stirred. The reaction was then heated to 80 C. After completion of the reaction, mixture was cooled to RT and extracted with ether. The combined organic layers were back-washed with H2O, dried (CaCl2), filtered and solvent was removed in vacuo to obtain 0.74 g (90%) of crude product. Title compound was dissolved in ether (20 ml) and passed through silica gel layer (30×30 mm). Silica gel was washed with ether several times, ether was removed in vacuo to obtain 0.67 g of 2,3-dimethyl-1,4-benzoquinone (HPLC purity 99.37%).

TLC: $R_f$ 0.46 (chloroform); HPLC: $\tau$=17.6 min (0-90% B for 26.4 min; A: 10 mM $H_3PO_4$; B: acetonitrile); M.p. 60° C.; UV (methanol): $\lambda_{max}$ 209 nm, 256 nm, 344 nm.

2,3-dimethyl-5-(10'-bromodecyl)-1,4-benzoquinone (3)

136 mg (1 mmol) of 2,3-dimethyl-1,4-benzoquinone (2) was dissolved in mixture of acetonitrile and H2O (10 ml, (1:1)). To solution obtained 292 mg (1.1 mmol) of 11-bromoundecanoic acid and silver nitrate (170 mg, 1 mmol) were added. Reaction mixture was heated to 60-70 C and solution of ammonium persulfate (228 mg, 1 mmol) in H2O (10 ml) was added dropwise. Reaction was heated at the same temperature for a further hour, then cooled and extracted with ether. The combined ether layers were back-washed with 5% sodium bicarbonate solution, dried ($MgSO_4$), filtered and solvent was removed in vacuo. The residue was purified by flash chromatography on silica gel. Title compound (3) was obtained as red oil (Yield—70%).

TLC: $R_f$ 0.62 (chloroform); HPLC: $\tau$=23 min (79-90% B for 26.4 min; A: 10 mM $H_3PO_4$; B: acetonitrile); UV (methanol): $\lambda_{max}$ 207 nm, 258 nm, 344 nm; MALDI-TOF MS: calc. for $C_{18}H_{27}O_2Br$: 355.3. found m/z 356.1 (MH$^+$; 100%); IR: 2928, 2336, 1600, 1496, 1304 sm$^{-1}$.

Rhodamine G Cesium Salt (4)

1 ml of 2M aqueous solution of cesium carbonate was added to a solution of rhodamine G (200 mg, 0.48 mmol) in methanol (6 ml). The product was filtered, washed with ether and dried in vacuo at 60 C. 210 mg (80%) of title compound (4) were obtained as dark-violet crystalline solid.

M.p.>250 C (dec.)

10-(2',3'-dimethyl-1',4'-benzoquinone-5'-decanoyl) rhodamine G

The compound (4) (190 mg) was suspended in DMF (5 ml) and to that the compound (3) (200 mg, 0.56 mmol) was added. The reaction was stirred at 50 C for 48 h and then concentrated in vacuo. The residue was purified by column chromatography on silica gel, eluting with chloroform-methanol (4:1). Fractions contained title compound were evaporated to dryness. To dry residue 5N HCl in dioxane (150 µl) was added, then evaporated and crystallized under benzene to yield 160 mg (65%) of title compound.

TLC: $R_f$ 0.68 (chloroform-methanol, 4:1); $R_f$ 0.80 (chloroform-methanol-$H_2O$, 65:25:4); HPLC: $\tau$=23.9 min (0-90% B for 26.4 min; A: 10 mM $H_3PO_4$; B: acetonitrile); M.p. 178-180 C (dec.); UV (methanol): $\lambda_{max}$ 250, 350, 535 nm, $\epsilon_{535}$=80000; Elemental analysis: calc. for $C_{44}H_{53}ClN_2O_5$: C, 72.86; H, 7.36; Cl, 4.89; N, 3.86. found: C, 72.53; H, 7.21; Cl, 4.22; N, 3.61. ES MS: calc. for $C_{44}H_{51}N_2O_5$ 688.89; found m/z 689.4 (MH$^+$; 100%). IR (film): 3200, 2928, 2336, 1700, 1685, 1600, 1496, 1304 sm$^{-1}$;

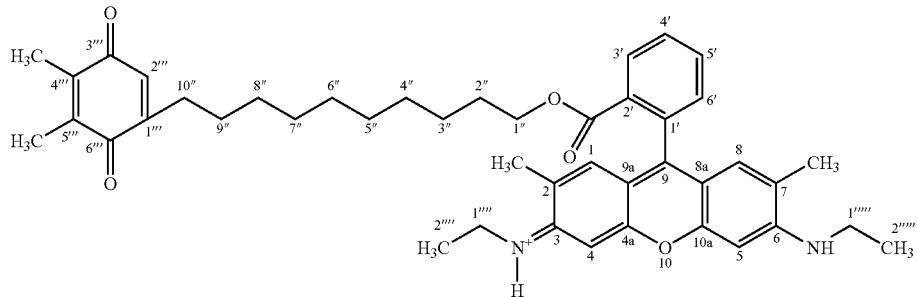 [SMILES: CCNc1cc2oc3c/c(=[NH+]/CC)c(C)cc-3c(-c3ccccc3C(=O)OCCCCCCCCCCC3=CC(=O)C(C)=C(C)C3=O)c2cc1C]

$^1$H-NMR (400 MHz; DMSO-$d_6$; atom numeration in structure as indicated above): 0.95-1.25 (brm, 14H, 2″, 3″, 4″, 5″, 6″, 7″, 8″ —(CH$_2$)$_7$); 1.24 (t, 6H, J=6.8 Hz, 2″″, 2″″″ —(CH$_3$)$_2$); 1.41 (q, 2H, J=7.5 Hz); 1.92 and 1.94 (each—s, 3H, 4‴, 5‴ —CH$_3$); 2.09 (s, 6H, 2.7 —(CH$_3$)$_2$); 3.48 (q, 4H, -1″″, 1″″″ —(CH$_2$)$_2$); 3.85 (t, 2H, J=6.3 Hz, 1″ —CH$_2$); 6.57 (s, 1H, H$_{3'}$); 6.80 and 6.91 (each—s, 3H, H$_1$, H$_5$ and H$_4$, H$_8$); 7.44 (dd, 1H; J$_1$=7.8, J$_2$=1 Hz; H$_{6'''}$); 7.74 (t, 2H, J=5.8 Hz; 3.6 —NH); 8.60-8.70 (m, 2H, H$_{4'''}$ and H$_{5'''}$); 8.22 (dd, 1H, J$_1$=8.2; J$_2$=1.1 Hz, H$_{3'''}$).

$^{13}$C-NMR (400 MHz; DMSO-$d_6$): 11.59 and 11.98 (4‴, 5‴ —(CH$_3$)$_2$); 13.45 (2″″ and 2″″″ —(CH$_3$)$_2$); 17.29 (2.7 —(CH$_3$)$_2$); 25.07, 27.29, 27.57, 28.25, 28.39, 28.51, 28.55, 28.56 and 28.65 (2″, 3″, 4″, 5″, 6″, 7″, 8″, 9″, 10″ —(CH$_2$)$_9$); 37.86 (1″″, 1″″″ —(N—CH$_2$)$_2$); 64.96 (1″ —CH$_2$); 93.45 (C$_4$ and C$_5$); 112.78 (C$_1$ and C$_8$); 125.32 (C$_{4'}$); 128.38 (C$_{5'}$); 129.78 and 130.75 (C$_{1'}$ and C$_{2'}$); 130.20 and 130.22 (C$_{5'}$, C$_{8a}$ and C$_{9a}$); 131.77 (C$_2$); 132.85 (C$_{9'''}$); 132.88 (C$_{3'}$); 139.79 and 140.36 (C$_{4'''}$ and C$_{5'''}$); 148.40 (C$_{1'''}$); 155.71 and 156.6 (C$_{4a}$-C$_{10a}$ and C$_{3'''}$-C$_{6'''}$); 164.98 (COOR); 186.91 and 187.00 (C$_{3'''}$ and C$_{6'''}$).

Compound SkQ1 is a compound of structure (I) (wherein A—fragment of plastoquinone—natural antioxidant from chloroplast thylakoid, B—triphenylphosphonium cation)

SkQ1 (2,3-dimethyl-4-benzoquinon-5-decyl-triphenylphosphonium bromide) was prepared analogously to method of example 1.

The synthesis of mitochondrially targeted antioxidant SkQ1 presented at Scheme 2:

Scheme 2

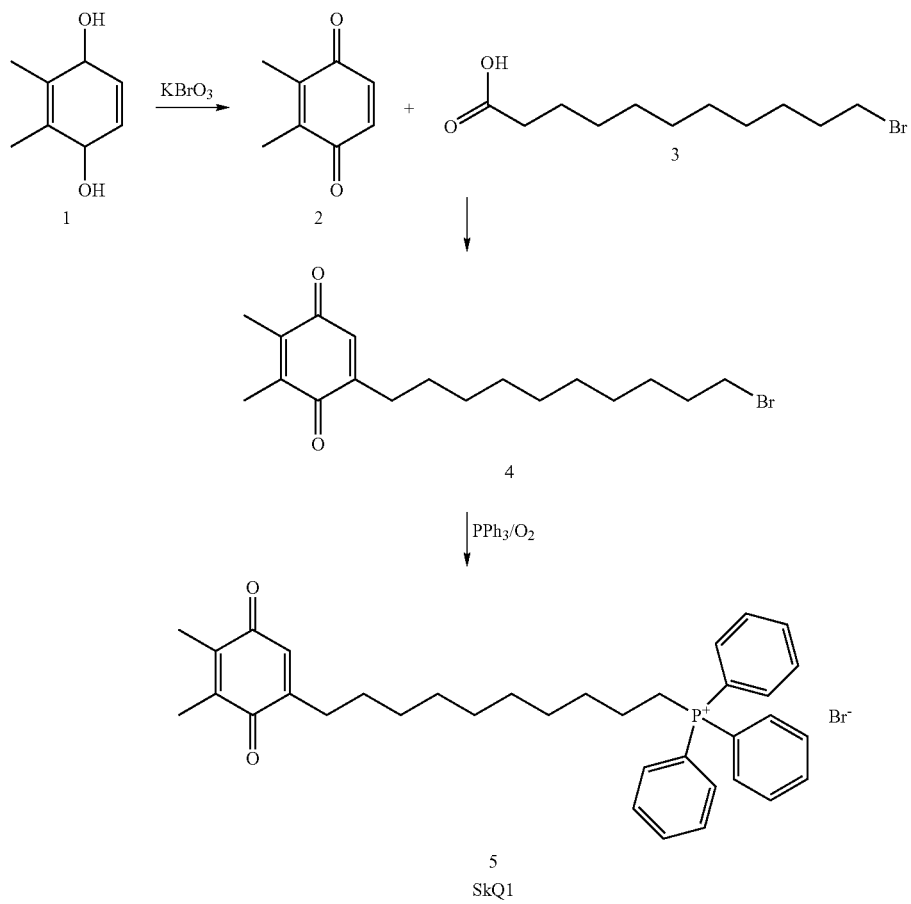

5
SkQ1

Method of preparation of 2,3-dimethyl-1,4-benzoquinon-5-decyl-triphenylphosphonium bromide (SkQ1) comprises:

1. Oxidation of 2,3-dimethylhydroquinone by potassium bromate to corresponding 2,3-dimethyl-1,4-benzoquinone (2).
2. Addition of 11-bromoundecanoic acid (3) to above-obtained 2,3-dimethyl-1,4-benzoquinone (2) in presence of silver nitrate and sodium persulfate.
3. Formation of title compound (5) in course of reaction of compound (5) with triphenylphosphine in oxygen atmosphere.

Title compound was obtained as highly hygroscopic tan solid (HPLC purity>95%, content of title compound is 98.55% (HPLC)).

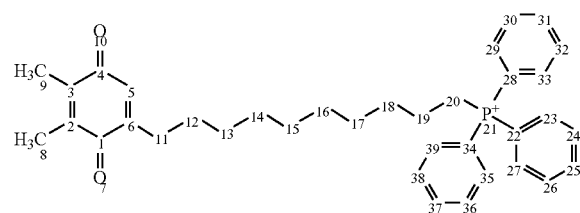

$^1$H-NMR (CDCl3; δ, ppm; atom numeration in structure as indicated above): 7.82-7.58 (m, 15H, aromatics); 6.38 (s, 1H, H-5); 3.6 (m, 2H, CH$_2$P(Ph)$_3$); 2.25 (m, 2H, CH$_2$CH$_2$CH$_2$CH$_2$CH$_2$CH$_2$CH$_2$CH$_2$CH$_2$CH$_2$P(Ph)$_3$); 1.90 (br s, 6H, CH$_3$) 1.55, 1.32, 1.15 (3m, 6H, 3CH$_2$).

HQSC (DMSO; δ, ppm): 8.15 (br s, 1H, tautomeric OH), 7.88-7.20 (m, 15H, aromatics); 7.08 (br s, 1H, tautomeric OH), 6.38 (s, 1H, H-5); 3.55 (m, 2H, CH$_2$P(Ph)$_3$); 2.4 (m, 2H, CH$_2$CH$_2$CH$_2$CH$_2$CH$_2$CH$_2$CH$_2$CH$_2$CH$_2$CH$_2$P(Ph)$_3$); 2.05, 1.90 (2s, each of 3H, CH$_3$); 1.5 (m, 6H), 3CH$_2$).

$^{13}$C-NMR (DMSO; δ, ppm): 147.83, 144.65 (C-1, C-4); 134.75-129.97 (Ph); 113.01 CH$_2$P(Ph)$_3$; 12.72, 11.89 (CH3).

ESI-MS (m/z): [M]$^+$ calc. 537.7. found 537.4.

Purity control was achieved by two methods: HPLC and NMR-spectrometry (500 MHz). There was a need to use two different methods because the title compound had pronounced surface-active characteristics, which makes difficult the chromatography of title compound.

Compound DMMQ (10-(2-methyl-5-methoxy-3,6-dioxo-1,4-cyclohexadienyl)-decyl-triphenylphosphonium bromide) was synthesized with the same method.

Compound DMMQ is a compound of structure (I) (wherein A—fragment of demethoxyubiquinone, B—triphenylphosphonium cation). Demethoxyubiquinone can interact with free radicals or reactive oxygen species, but cannot be reduced by mitochondrial respiratory chain, and so possesses prooxidant, cytotoxic characteristics.

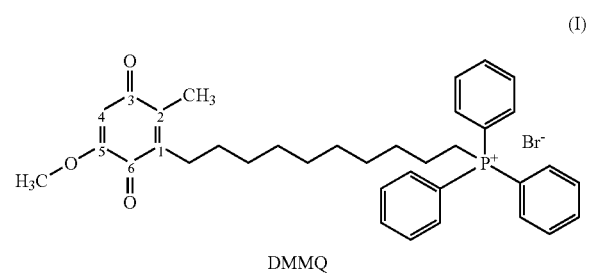

DMMQ

Experimental Example 2

Transfer of the Compounds of Structure (I) Across the Planar Lipid Membrane It was shown that the test compound of structure I (compound SkQ1 was used) penetrates the planar bilayer phospholipid membrane down to concentration gradient and distributes across the membrane according to the Nernst equation. Therefore, SkQ1 is a penetrating cation.

The experimental method has been used several times before in the experiments aimed at the exploring of an ability of different ions to penetrate the planar bilayer lipid membrane and is described in details Liberman E A, Topaly V P, Tsofina L M, Jasaitis A A, Skulachev V P., 1969, Nature, 222, 1076-8. This method includes the use of two chambers filled in with water-based solution and separated by bilayer membrane, also the electrometrical registration of transfer of charged compounds capable of penetration across such membrane from one chamber to another.

In our experiment the membrane was made of mixture of phosphotydilcholine and diphytanoyl derivative of lecitin dissolved in decane; both chambers were filled with 50 mM TrisHCl, pH 7.4 containing $10^{-7}$ M SkQ1. Then the concentration of SkQ1 in of the chambers was gradually increased from $10^{-7}$ M to $10^{-5}$ M. It was shown that such an increase resulted in generation of an electric potential difference in accordance with Nernst equation for ideal membrane-penetrating cation (FIG. 1). On the other hand, Nernst equation was not applicable for lower the SkQ1 concentrations below $10^{-7}$ M.

Thus, compound SkQ1 (2,3-dimethyl-1,4-benzoquinone-5-decyl-triphenylphosphonium) is a lipophilic substance capable of penetration across biological membranes in its cationic form.

Experimental Example 3

Antioxidant Properties of the Compounds Corresponding to Structure (I)

It was shown that the test compound corresponding to structure (I)—mitochondrial antioxidant SkQ1 is a very effective antioxidant having much higher antioxidant activity than that of the previously described antioxidants, claimed as "mitochondrially targeted" in an invention U.S. Pat. No. 6,331,532 (compound MitoQ).

Figure 2:
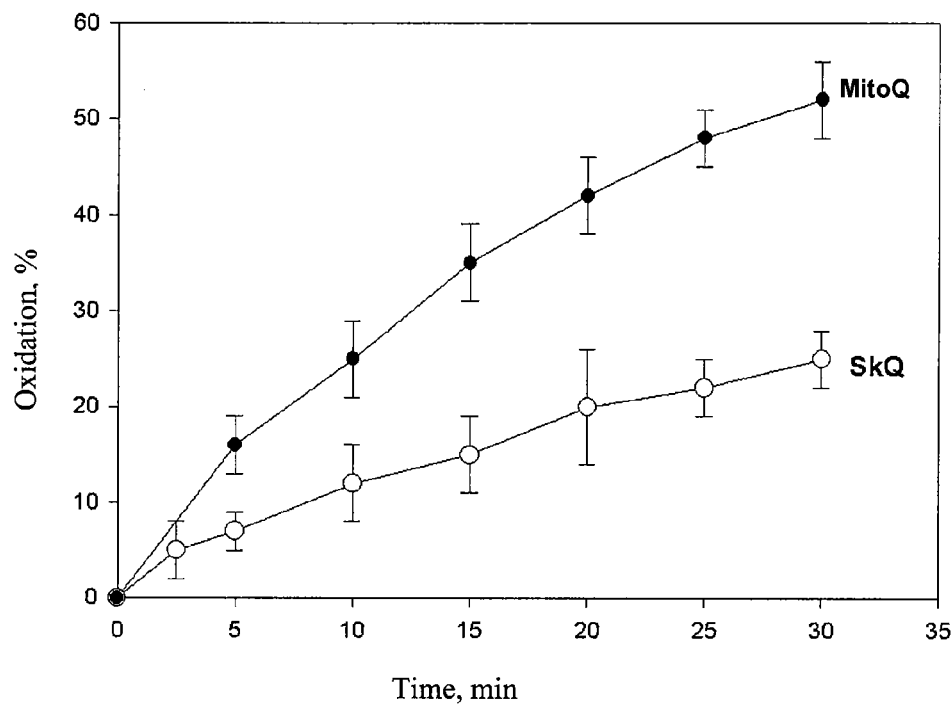
FIG. 2 demonstrates the spontaneous oxidation of quinol derivatives of MitoQ and SkQ1.

Stability of the reduced (quinols) forms of SkQ1 and MitoQ under aerobic conditions was examined by analysis of the absolute absorption spectra of these compounds in a range from 240 to 310 nm using double-beam spectrophotometer Pye Unicam SP1100, England. Quinone derivatives were reduced with sodium tetrahydroborate in the medium containing 20 mM MOPS-KOH, pH=7.6. Control cuvette did not contain SkQ1 or MitoQ, reductant was added to both cuvettes, measurements were carried out just after the hydrogen release ceased. The level of reduced quinones was estimated by the size of peak area using the weighing method; absolute absorption value at 267 nm (maximum absorption) was used as a control. It can be seen from FIG. 2 that the of autooxidation of the reduced (quinol) form of SkQ1 by air oxygen is about three-fold lower than that of MitoQ.

Figure 3:
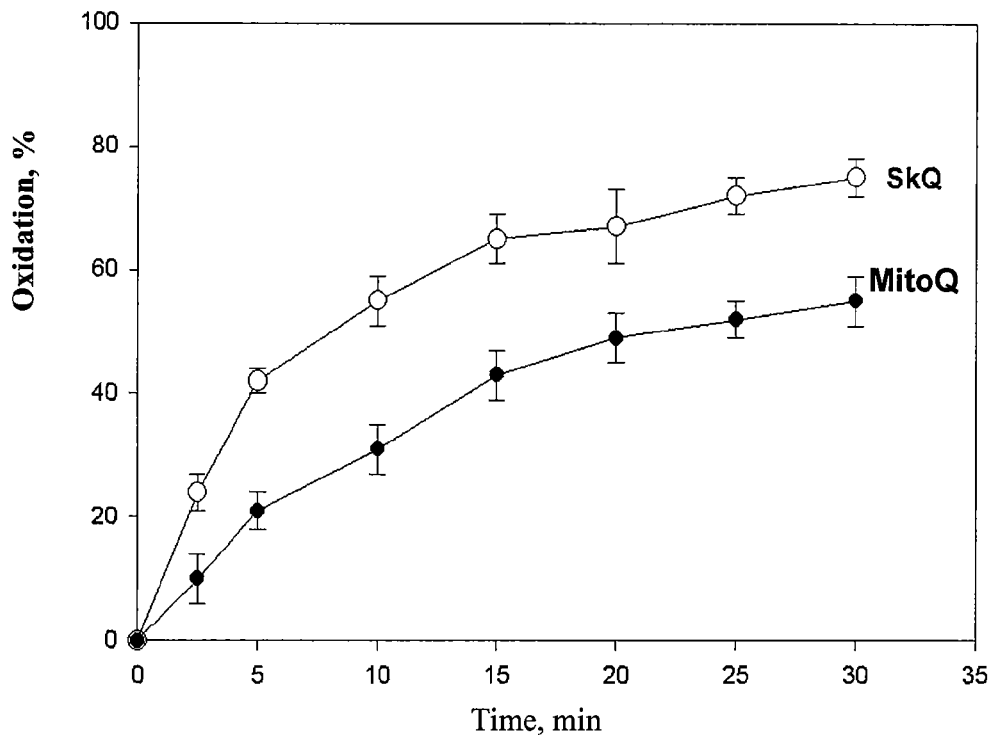
FIG. 3 shows the increase of the oxidation rate of "MitoQ" and "SkQ1" quinol derivatives upon addition of the superoxide radical into the system. A—oxidation rate of the reduced forms with both air oxygen and superoxide radical; B—oxidation rate of the reduced forms with superoxide radical only.
Figure 3:
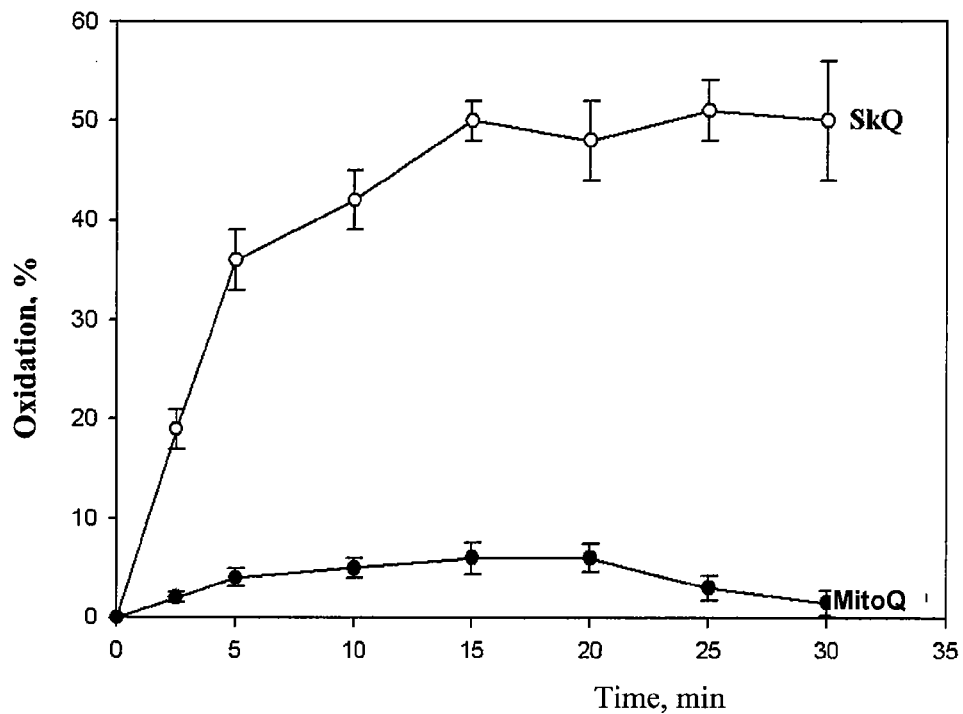

In order to compare antioxidant activity of the reduced forms, we measured the oxidation rate of quinols by superoxide-anion radicals generated in xanthine oxidase/hypoxanthine system. It can be seen from FIG. 3a that the oxidation rate of SkQ1 in the presence of both air oxygen and superoxide radical is about two times higher than that of MitoQ. FIG. 3b shows the oxidation rate of the quinol forms by superoxide radical, the oxidation rate by air oxygen being subtracted. It can be seen that SkQ1 interacts with superoxide radical very much faster than MitoQ.

The above experiments obviously demonstrate that SkQ1 possesses much better antioxidant properties than its analogue disclosed by the prior art. SkQ1 reacts (i) much faster with superoxide radical, the primary form of ROS, and (ii) much slower with air oxygen, resulting in the superoxide radical formation.

Experimental Example 4

Investigation of the Interaction of Mitochondria with Compounds of Structure (I)

The key advantage of the mitochondrially targeted antioxidants provided in this invention is their ability to be reduced by the respiratory chain of mitochondria. This is the essential distinction of these compounds from traditional antioxidants i.e. possibility of the safe neutralization of radical forms of the invented compounds and hence the possibility of the repeated neutralization of free radicals (FR) and ROS over and over again.

In order to examine whether the test compounds (SkQ1 and MitoQ) can be reduced by the respiratory chain of mitochondria, changes of the ratio between oxidized and reduced forms of test compounds were measured in the presence of respiratory substrates in a medium used for isolation of rat liver mitochondria. The measurements were carried out in the presence of mitochondria (protein concentration 0.2 mg/ml).

Figure 4:
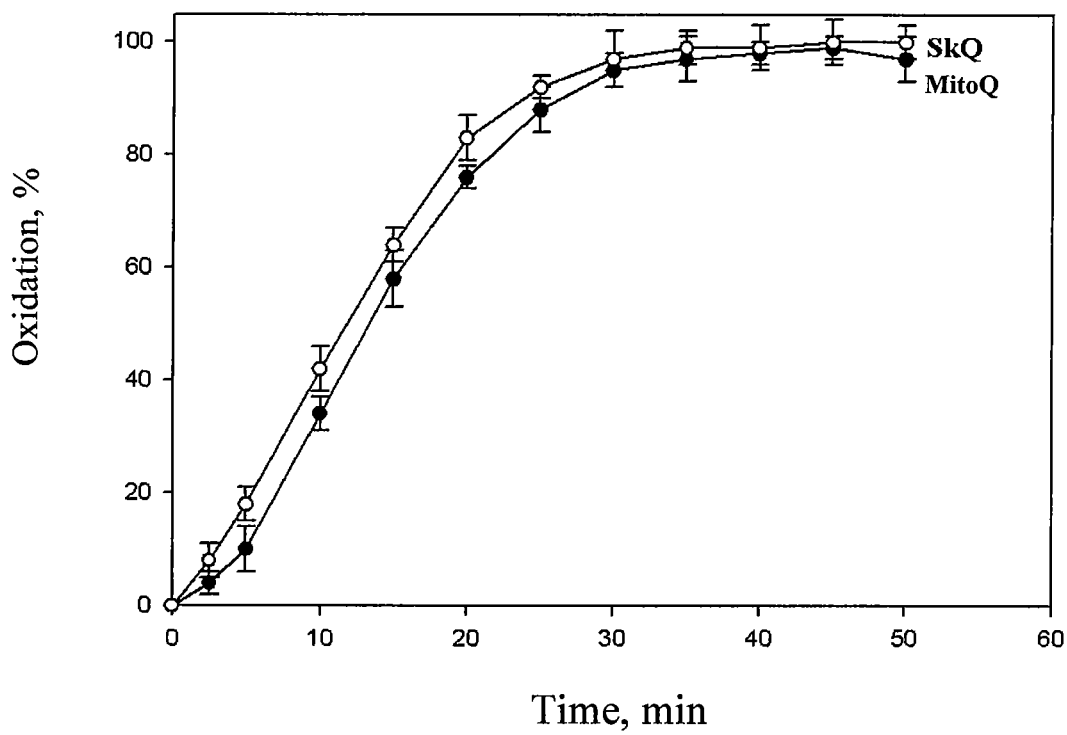
FIG. 4 shows the reduction of "MitoQ" and "SkQ1" by respiratory chain of rat liver mitochondria (0.2 mg/ml protein) energized with succinate (5 mM) in the presence of 2 $\mu$M rotenone.
Figure 5:
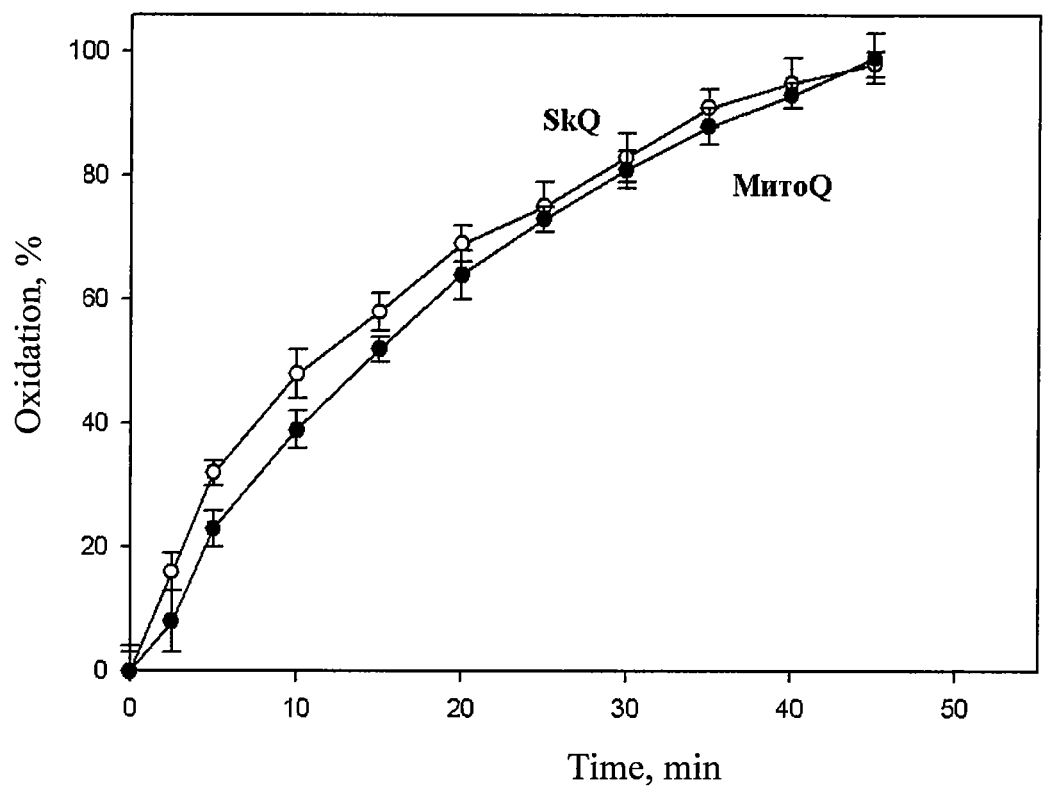
FIG. 5 describes the oxidation of quinols of "MitoQ" and "SkQ1" by respiratory chain of rat liver mitochondria energized with succinate (5 mM) in the presence of 2 $\mu$M rotenone. After complete reduction of quinol derivatives the respiratory chain was blocked with 25 mM malonate and reoxidation rate of "MitoQ" and "SkQ1" was measured.

The data obtained (FIGS. 4,5) indicate that both test compounds are readily reduced by energized mitochondria at the same rates and subsequently oxidized at rates that are much higher than that of spontaneous oxidation with air oxygen.

Moreover this experimental example shows that SkQ1 does not suppress the mitochondrial respiration at concentrations up to 10 μM. It was also shown that SkQ1 retains intact under incubation conditions in biological media during at least tens of minutes (during the whole experiment). These data indicate that SkQ1 has obvious advantages comparing to MitoQ as a ROS scavenger.

Experimental Example 5

Comparison of the Toxicity of Different Mitochondrial Antioxidants for Cells in Culture This experimental example compares the toxicity levels of mitochondrial antioxidant MitoQ, disclosed in the prior art, and the compound SkQ1 provided by this invention.

Figure 6:
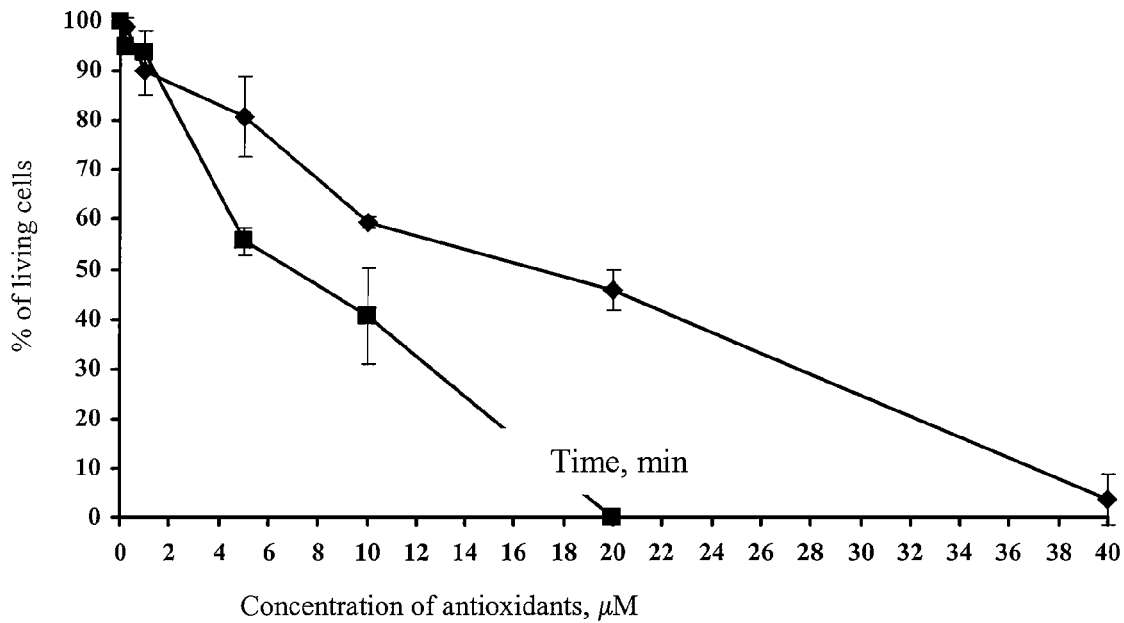
FIG. 6 shows the cytotoxic effect of "MitoQ" and "SkQ1" on Hela cells. % of living cells is proportional to O.D. (at 492 nm) of MTT-formazan.
Figure 7:
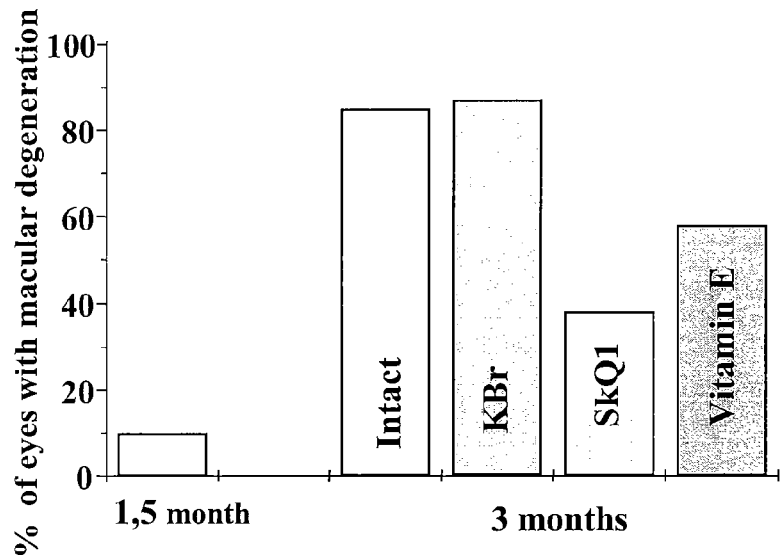
FIG. 7 shows the influence of SkQ and some other compounds on the development of retina degeneration in OXYS rats. % of eyes having degenerative changes in macular region of retina is at Y-axis.

SkQ1 and MitoQ at equal concentrations were added to cell cultures and the percentage of living cells was calculated after 2 h of incubation. Results shown in FIG. 6 demonstrate that SkQ1 has substantially lower toxicity. LD50 (concentrations at which 50% cells die) for SkQ1 and MitoQ was 20 μM and 7 μM respectively. This is also confirmed by the experiment where the toxic effects of SkQ1 and MitoQ on cells in the presence of hydrogen peroxide (at concentrations of 50, 100 and 200 μM) were tested. As in the previous case MitoQ appeared to be more toxic than SkQ1. LD50 of MitoQ in the presence of 100 μM hydrogen peroxide was 4 μM whereas that of SkQ1 was 20 μM i.e. was equal to LD50 of SkQ1 without hydrogen peroxide added. This difference can be easily explained by results obtained in experimental example 3 where the higher antioxidant and lower prooxidant properties of SkQ1 as compared to MitoQ were demonstrated.

Thus we can conclude that the mitochondrial antioxidants of structure (I) provided in this invention have much lower toxicity in comparison to the compounds known in the art and claimed as mitochondrial antioxidants.

Experimental Example 6

Protective Effect of the Compounds Corresponding to Structure (I) on Human Cells of Different Types In this example we show that compound of structure (I) with antioxidant function (mitochondrially targeted antioxidant) protects cultured cells from oxidative stress caused by $H_2O_2$.

Normal diploid fibroblasts from human skin and lung, human uterus carcinoma cells (HeLa cells) and human lymphoma cells (U 937 strain) were used in this experiment. Cells were cultivated in standard media (DMEM or RPMI) in the presence of 10% fetal serum at 37° C. and 5% $CO_2$. Experiments were carried out on the cultured cells grown to 30-50% confluency. $H_2O_2$ was added once and the cells were analyzed after 18-24 h of incubation. Apoptotic death was monitored by condensation of chromatin and nucleus fragmentation after staining the cells with Hoechst 33342 (1 μg/ml, 15 min). 300-500 cells were taken into account from each preparation and the final results are the average of 3-5 independent experiments. Necrosis was determined by staining of nuclei with propidium iodide (2 μg/ml, 5 min).

In the preliminary experiments concentrations of $H_2O_2$ causing considerable apoptosis (60-80%) with no detectable necrosis in different cell types were determined as 50-200 μM. It was confirmed that apoptosis in all cases was accompanied with decrease of mitochondrial membrane potential, release of cytochrome c from mitochondria into cytoplasm and activation of caspases.

In the experiments with antioxidant SkQ1 we determined the optimal conditions for protective antiapoptotic effect. It was shown that the incubation of cells with 20 nM SkQ1 during 6-day period greatly increases resistance of cells to $H_2O_2$. There was no need in the presence of antioxidant in the medium for incubation with $H_2O_2$ and this presence itself did not enhance the protective effect. In particular in the experiments with human lung fibroblasts hydrogen peroxide at concentration of 100 μM caused 60±5% apoptosis among cell population while preincubation with 20 nM SkQ1 lowered this value to 7±3%. Almost complete protection was observed also at concentration of $H_2O_2$ of 200 μM (80±5% apoptosis in control and 12±5% apoptosis after preincubation with 20 nM SkQ1). Protective effect of SkQ1 was retained when the concentration of $H_2O_2$ had been increased up to 500 μM but on the other hand there was a total death of cells by necrosis under such conditions. Almost the same results were obtained for all cell types tested.

Thus the extremely low concentrations of antioxidants of SkQ1 type effectively protect the cells of different types from apoptosis caused by oxidative stress. Therefore such compounds and corresponding compositions containing them must be effective for the prevention of programmed cell death in different tissues, organs, the whole body. This discovered property of SkQ may be used for therapy and prophylaxis of diseases where decrease of oxidative stress and/or prevention of the programmed cell death is an effective therapeutic method.

Experimental Example 7

Prevention of Apoptotic Signal Transduction by the Compounds of Structure (I) (Long-Distance Transmission of the Apoptotic Signal Between Cells is Blocked by the Antioxidants of SkQ1 Type)

HeLa cells were used in these experiments. Cells grown on a glass slide were treated with different apoptosis-inducing agents (tumor necrosis factor (TNF), staurosporine, $H_2O_2$) for 3 h. Then the glass slide with cells (inducer) was washed to remove these reagents and placed into Petri plate to come into contact with glass slide (recipient) with cells grown in the absence of any apoptosis-inducing agent. After 16-18 h of subsequent growth and staining the cells with Hoechst 33342 as described above, apoptosis at both glass slides was analyzed.

Preliminary experiments showed that when apoptosis at slide-inducer was about 80-90% then 30-50% of cells at slide-recipient also revealed apoptotic morphology. Control experiments demonstrated that there was no transmission of initial apoptosis-inducing agent to recipient cells in this model. Transmission of the apoptotic signal did not require direct contact of cells and was less efficient when incubation medium volume increased. Addition of catalase (2500 E/ml) into the medium for joint incubation prevented apoptosis of recipient cells and at the same time had no significant influence on the apoptosis (caused by TNF or staurosporine) of inductor cells. Thus the main mediator of apoptosis signal was $H_2O_2$.

Incubation of inductor cells with 20 nM SkQ1 for 6 days did not prevent the apoptosis caused by TNF (10-50 ng/ml, with addition of 1 µM emetine) or staurosporine (2 µM). After putting both glass slides into contact and subsequent incubation apoptosis caused by TNF at slide-inducer was 95±5% in control and 90±5% after incubation with SkQ1. Apoptosis at slide-recipient was 37±4% in control and 17±3% after preincubation of inducer with SkQ1. It must be taken into account that apoptosis in control experiment with no TNF added was 12±3% at both slides because of the toxic effect of emetine. Therefore protective effect of SkQ1 was almost 100%. Preincubation of recipient cells with SkQ1 gave similar results. In this case apoptosis has been lowered to 16±4%. The same protective effect was also observed for induction of apoptosis with staurosporine.

Measurements showed that the joint incubation of inductor cells (pretreated with TNF) and recipients cells resulted in significant increase of $H_2O_2$ concentration in the medium (as compared to control where non-treated cells were incubated) 2-3 h after putting the slides into contact. $H_2O_2$ concentration was 140±20 nM 24 hours later whereas it was just 40±10 nM if inductor cells had been preincubated with SkQ1. Preincubation of recipient cells with SkQ1 did not lead to decrease of $H_2O_2$ concentration.

Thus the extremely low concentrations of antioxidants of SkQ1 type block generation of apoptotic signal by cells which were treated with apoptosis-inducing agents of different nature. The same antioxidants effectively protect recipient cells from apoptosis caused by the signal going from inductor cells through the medium.

Transmission of apoptotic signal may underlie pathogenesis of diseases (infarction, stroke, posttraumatic pathologies) in which injured tissue parts are surrounded by the enlarging zone of apoptotic cells.

Experimental Example 8

Protective Effect of the Compounds of Structure (I) Against Photodynamic Damage of Cells Antioxidants of SkQ1 type inhibit the toxic effect of singlet oxygen generated by photoactivation of photosensitizers and prevent necrotic cell death caused by photodynamic treatment of mitochondria.

Protection from the damaging effect of singlet oxygen was analyzed using model lipid membrane containing gramicidin and phthalocyanine photosensitizer. Measurements of the current of ions through gramicidin channel showed that the activation of photosensitizer with a short flash of light resulted in rapid inactivation of the channel. This effect was blocked by sodium azide, which indicated that singlet oxygen was the main factor in the inactivation of gramicidin.

Protection from photodynamic treatment was studied using cultured HeLa cells. Cells were incubated with photosensitizer chloromethyl-X-rosamine (0.5 µM, 15 min) which was then selectively accumulated within mitochondria. Cells were photoirradiated with green light (at maximum absorption for photosensitizer of 580 nM) through the objective of microscope Axiovert 200M (Zeiss, Germany) for 1-2 min and analyzed 5 h later. Necrosis was determined by staining of nuclei with propidium iodide (2 µg/ml, 5 min).

It was found that SkQ1 at 1 µM concentration completely prevents light-dependent inactivation of gramicidin in the model lipid membrane containing phthalocyanine photo sensitizer.

There was 100% necrotic cell death after photodynamic treatment of cells. On the other hand necrosis from photodynamic treatment was 25±5% if the cells had been preincubated with 20 nM SkQ1 for 6 days. When 1 µM SkQ1 was added 1 h before the photoirradiation necrotic cell death was 15±5%. The increase of SkQ1 concentration did not provide additional protection whereas decrease to 0.5 µM led to substantial decrease of the effect.

It can be clearly seen from these results that the extremely low concentrations of antioxidants of SkQ1 type prevent the damaging effect of singlet oxygen generated by photoirradiation of the photosensitizers. Such antioxidants effectively protect the cells from necrosis caused by photodynamic treatment if the photosensitizer is located within mitochondria.

Experimental Example 9

Protective Effect of Compounds of Structure (I) Against Aging-Related Cataract and Macular Dystrophy The increase of the average human life-span in developed countries results in the progressive aging of the world's population and is accompanied by the growth in age-related diseases, among which macular dystrophy and cataract take the third place after cancer and osteoporosis according to the recent reports of WHO/OMS. Because cataract and macular degeneration are the main reasons for blindness in people over the age of 55, the determination of the risk factors for these diseases and the development of reliable prophylactic treatments are of great economic importance. The effect of diet on the development of cataract and macular dystrophy has been actively discussed in literature. The age-related eye disease study showed a significant reduction in the relative risk of developing age-related macular degeneration in patients obtaining antioxidants for long time. However, according to epidemiologic data antioxidant supplementation can significantly decrease macular dystrophy and cataract but cannot fully stop the development of these pathologies.

There is a rapidly growing number of pharmacological agents and bioactive nutrients, which have been reported to possess antioxidant activity. However, the objective evaluation of the antioxidant efficiency remains difficult because of the late detection and individual features of pathogenesis of these diseases. Traditionally, animal models enable researchers to study the effects of antioxidants. Our recent investigations showed that the strain of senescence-accelerated OXYS rats, which possesses the features of aged animals, also constitutes the unique genetic model of eye ageing and therefore gives the unique possibilities for correct evaluation of antioxidant efficiency. The OXYS strain of rats was developed at the Institute of Cytology and Genetics, Russian Academy of Sciences, from Wistar stock by selection for their susceptibility to the cataractogenic effect of galactose. Genetically determined defects in several metabolic pathways make the animals of this strain highly sensitive to oxidative stress and result in the development of accelerated senescence syndrome. Pathological alterations in the lenses of OXYS rats occur as early as at the age of 2 months, and in 6 months cataract is detected in almost 100% of tested animals (compared to 5% in Wistar rats) and in 12 months cataract affects both eyes. According to ophthalmoscopic, biomicroscopic and morphological data cataract in OXYS rats corresponds to human senile cataract and develops in close conjunction with progressive macula dystrophy. The early signs of macular degeneration are manifested in 6 weeks of age and to the age of 4-6 months the pathology reaches the pronounced stages. By manifestation of features, the pattern of eye-ground lesions in OXYS rats corresponds to the retina alterations observed in human patients with macular dystrophy such as central involutive chorioretinal degeneration.

The goal of the present part of the invention was to investigate the effect of SkQ chemical on the development of cataract and macular dystrophy in OXYS rats.

The study was carried out using a total of 120 male OXYS and Wistar rats. The animals were housed in cages (45*35*35 cm) and kept under standard laboratory conditions (at 22±1° C., 60% relative humidity, and natural light), provided with a standard rodent diet (PK-120-1, Ltd. 'Laboratorsnab', Russia), and given water ad libitum. At the age of 1.5 months after preliminary pupil dilation with 1% tropicamide ophthalmic the rats were conducted through ophthalmoscopic examination using direct ophthalmoscop "Betta", Germany. During the period from 1.5 to 3 months, which is critical for the development of pronounced changes in eye organ of OXYS rats, the animals were given either SkQ1 (50 nmol per kg of body weight), or KBr (50 nmol per kg of body weight) or vitamin E (alfa-tocopherol acetate, 20 mg per kg). We use Vitamin E for a comparison with test antioxidants. Animals received the compounds on a small piece of dried bread before a regular meal, and the control group of animals received the same piece of bread without any compound. After completing the course of antioxidants the animals were retested with ophthalmoscope. To avoid human factor in the evaluation of compound effects the researcher who conducted the ophthalmoscopic examination was not told which of the animals received antioxidants.

The lens state was evaluated according to the classification system accepted in clinical practice with grades ranging from 0 to 3: score 0—the lens is clear; score 1—spotted weak cloudiness; score 2—multiple spots of cloudiness and score 3—intense cloudiness of the lens core and nucleus. The presence and the degree of spotted changes in macular area were evaluated according to accepted classification: score 0—no changes; score 1—the $1^{st}$ stage of pathology, when small yellow deposits, known as "drusen" appear underneath the macula; score 2—$2^{nd}$ stage, the development of prominent yellow spot with sharp edges with the size of 0.5 to 1 of the disk diameter (exudative exfoliation of pigmented retinal epithelium); and score 3—$3^{rd}$ stage with extensive hemorrhage into macular area.

Results

Ophthalmoscopic examination did not reveal any changes in the lenses or in the macular area of the retina in 1.5 and 3 month-old Wistar rats. In OXYS rats on the contrary early cataract (score 1) was observed in 20% of cases and macular degeneration of the $1^{st}$ stage—in 10% of cases at the age of 1.5-months.

Figure 8:
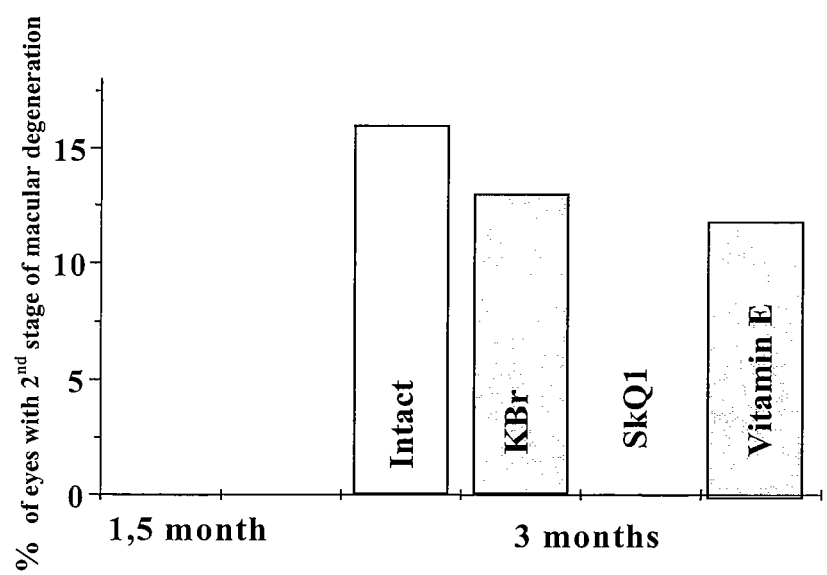
FIG. 8 shows the percentage of eyes with macula changes of the 2nd stage. Administering of SkQ1 not only decreased the morbidity of maculodistrophy but also reduced degree of macula changes substantially. % of eyes with maculodistrophy of the 2nd stage is at Y-axis.
Figure 9:
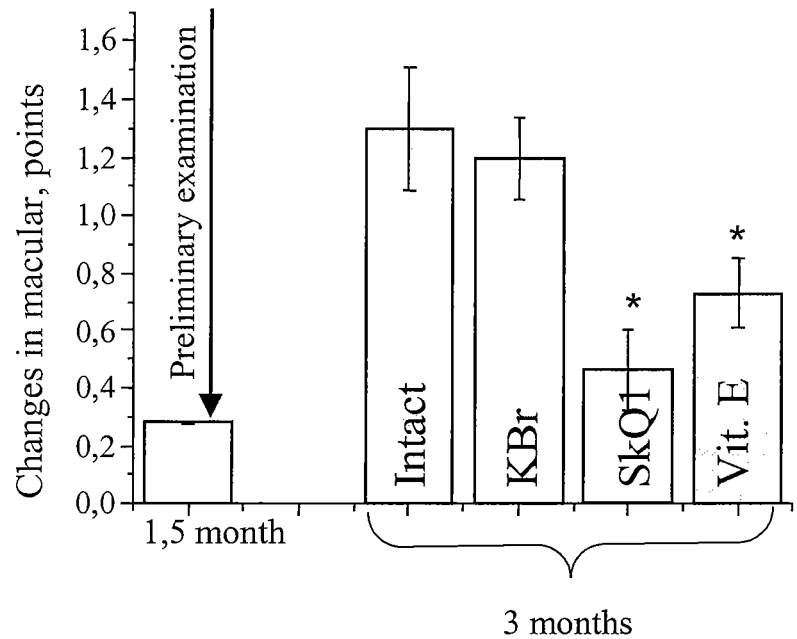
FIG. 9 shows degenerative changes in macular region of retina of OXYS rats before administering and after 45-day course of KBr, SkQ1 and vitamin E.
Figure 10:
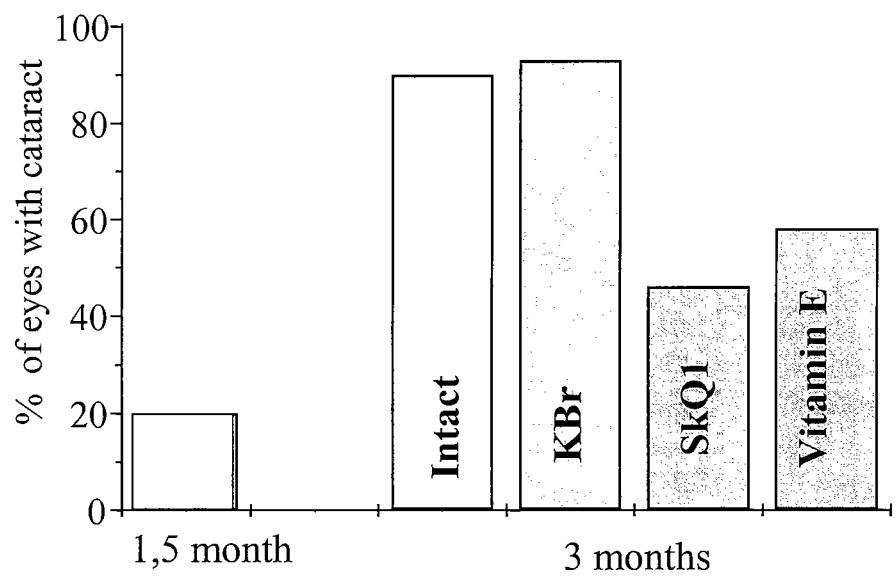
FIG. 10 describes the influence of SkQ1 and some other compounds on the cataract morbidity in OXYS rats. % of eyes having changes of crystalline lens is at Y-axis.
Figure 11:
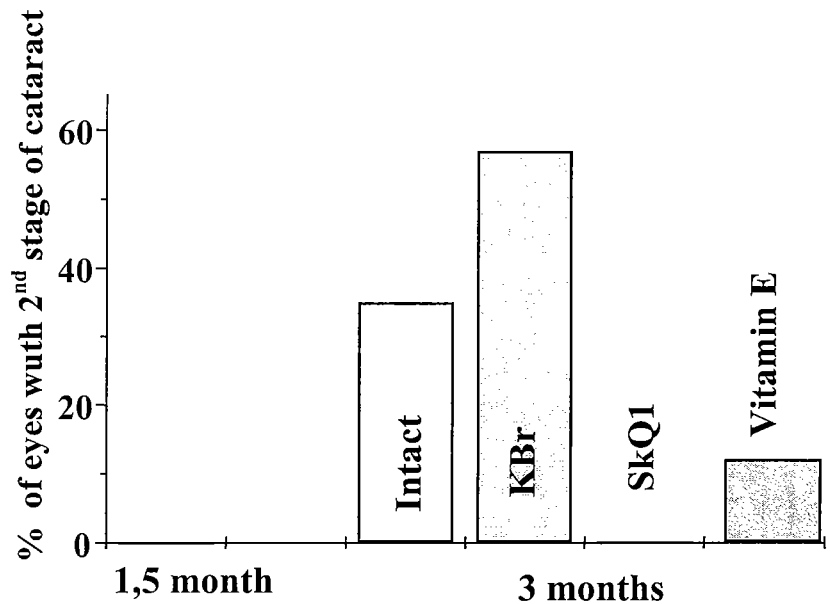
FIG. 11 shows the percentage of eyes with crystalline lens changes of the 2nd stage. Administering of SkQ1 not only decreased the morbidity but also reduced degree of cataract substantially. % of eyes with changes corresponding to the 2nd stage of disease is at Y-axis.
Figure 12:
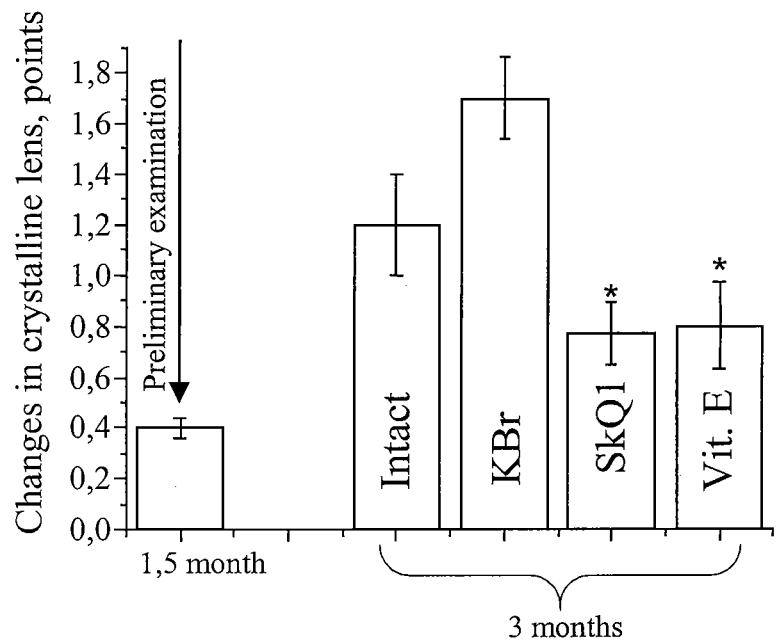
FIG. 12 shows the condition of crystalline lens of OXYS rats before administering and after 45-day course of KBr, SkQ1 and vitamin E.

At the age of 3 months in the control intact group of OXYS rats pathological changes of lenses were observed in 90% of examined eyes, including 35% of eyes with $2^{nd}$ stage of cataract. Macular dystrophy was observed in 85% of eyes from control group of animals of which 16% corresponded to the $2^{nd}$ stage of this pathology (FIG. 8).

In the group of OXYS rats supplemented with KBr lens changes were observed in 93% of eyes with 57% of total number of eyes having $2^{nd}$ stage of cataract development. Changes in the macular area of the retina were observed in 87% of eyes of animals from this group and 13% of these changes corresponded to the $2^{nd}$ stage of the disease.

In animals supplemented with SkQ1 some lens changes were registered in 46% of cases, and all of them were defined as the $1^{st}$ stage of cataract. Changes in the macular area of the retina in OXYS rats of this group were revealed in 38% of cases and also were defined as the $1^{st}$ stage of macular degeneration.

In the group of animals, supplemented with vitamin E, lens changes were registered in 58% of cases, with 12% of changes corresponding to the $2^{nd}$ stage of the cataract. Changes in the macular area of the retina were revealed in 54% of OXYS rats from this group, including 8% corresponding to the $2^{nd}$ stage of macular degeneration. The results of these experiments are shown in FIG. 7-12 in graphical form.

Thus, this experimental example proves the efficiency of SkQ1 application for prophylactics of age-related eye diseases. Therefore, the results also confirm the efficiency of mitochondrial antioxidants corresponding to the structure (I) in the defense against diseases associated with oxidative stress.

Experimental Example 10

Protective Action of Mitochondrial Antioxidant SkQ1 on a Cardiac Muscle

It is known that reactive oxygen species (ROS) have regulatory or toxic effects on a cardiac muscle depending on their concentrations. When studying SkQ1 compound its ability to modulate ROS action has been found. Experiments have been carried out in the isolated hearts of rats which were given SkQ1 intravenously or with nutrition (50 μg/kg). The heart was isolated 2 hours after intravenous introduction of the compound, or after 2-week nutritional supplementation. The heart was perfused retrogradely according to a standard procedure by Krebs solution with a constant rate, and perfusion pressure (PP) characterized the tonus of coronary arteries. A spontaneous heart rate and isovolumic pressure in a left ventricular latex balloon were also recorded. These parameters were monitored at 40-minute introduction of 150 mcM $H_2O_2$, a standard ROS generator.

In experiments with a single intravenous SkQ1 introduction, a two-fold increase in perfusion rate was followed in this and control groups by approximately equal perfusion pressure rise to 120-125 mmHg. A $H_2O_2$ introduction has usual biphasic effect on PP: an initial PP decline was followed by its increase. In the control group the minimal PP level has reached 95±5 mmHg, and in the group receiving SkQ1–77±2 mm Hg (p<0.02). Maximal PP decline in comparison with an initial level before $H_2O_2$ introduction was −28±3 mmHg and −43±5 mmHg on the average respectively (p<0.05). In experiments with prolonged SkQ1 consumption, the maximal PP decline in the control group was in average −21±5 mmHg on the average, and in the group receiving SkQ1 −38±5 mmHg (p<0.03). The significant difference between groups was also kept at the end of $H_2O_2$ introduction −5±6 mm Hg and −29±6 mmHg, respectively (p<0.03). Thus, both single and prolonged SkQ1 application potentiated the initial vasodilatatory effect of $H_2O_2$, besides, at prolonged application the SkQ1 compound decreased toxic $H_2O_2$ action on coronary vessels.

Thus, it is possible to conclude, that SkQ1 compound potentiates regulatory and reduces toxic ROS action on coronary vessels of the isolated heart. This action of SkQ1 can be used for therapy or prophylactics of cardiovascular diseases.

Experimental Example 11

Effect of the Compounds of Structure (I) on the Morphology and Mobility of the Normal and Tumor Cells Antioxidants of SkQ1 type cause morphological changes of the cultured cells resulting in decrease of their mobility and increase of adhesion to surface.

Normal fibroblasts from the human skin and lung and HeLa cells were cultivated at low cell density (20-30% confluency). Morphometric measurements were carried out for cell area, dispersion and elongation. Cytoskeleton structures were analyzed by staining the fixed cell preparations with rhodamine falloidin (actin filaments), antibodies against tubulin (microtubules) and vinculin (surface contacts). Mobility of the cells was examined with the help of microvideo camera.

Fibroblasts revealed highly changed morphology after pre-incubation with 20 nM SkQ1 for 6 days. Mean cell area was 2.9 times higher, dispersion index lowered by factor 2.4 and elongation index decreased from 2.34 to 0.69. The amount of actin filaments was 3.7 times higher thus giving 136% filament density in comparison to the control. Actin filaments assembled into large bundles—stress fibrils. The number of contacts with surface greatly increased. Mobility of fibroblasts was distinctly lower. All these changes had no influence on the rate of fibroblast proliferation. The same measurements of HeLa cells showed that their mean area was 2.6 times higher (with no changes in dispersion and elongation), the amount of actin filaments was increased while the mean density of filaments was not changed.

Therefore the morphological changes of cells and decrease of their mobility in response to the treatment with antioxidants of SkQ1 type indicate the reduction in migratory ability and metastasis formation.

Experimental Example 12

Cytotoxic Effect of the Compounds Corresponding to Structure (I) on Tumor Cells

Compounds corresponding to structure (I) and having prooxidant and protein-modifying activities can induce the opening of non-selective pore in mitochondria, mitochondria swelling, release of cytochrome c from the intermembrane space into cytoplasm and apoptosis. Mitochondrially-targeted inhibitors of the antiapoptotic proteins may promote the apoptosis caused by these compounds and chemotherapeutic drugs known in the art.

It was shown that prooxidants and compounds interacting with vicinal dithiols (phenylarsine oxide, PAO) induce the opening of non-selective pore and swelling of mitochondria in cells and cell-free system. In particular, induction of the mitochondrial pore with PAO in the experiments with tymus lymphocytes led to release of $Ca^{2+}$ ions from mitochondria into cytoplasm. By using electron microscopy, mitochondria with swollen matrix were observed in these cells. PAO possesses a high non-specific toxicity which does not allow PAO usage in investigation of the mechanism of cytochrome c release and resulted apoptosis. It was shown in some cell models that the agents inducing the pore opening also promote release of cytochrome c into cytoplasm and apoptosis. It may be assumed that the mitochondria-specific targeting of PAO and similar compounds would decrease their non-specific toxicity and allow the induction of apoptosis in target cells. It was previously shown that compounds bearing the positive charge (phosphonium and rhodamine derivatives) accumulated and stayed in mitochondria of the fast-growing tumor cells much more effectively than in mitochondria of the normal cells. Taking into account the above information we can conclude that production of the effective and specific anticancer drugs based on the compounds corresponding to structure (I) is more than possible.

Experimental Example 13

Anticancer Effect of the Compounds of Structure (I) Against Ascite Carcinoma

In order to test whether the compounds of structure (I) can be used for treatment of oncological diseases, an effect of SkQ1 on mice with acquired Ehrlich ascite carcinoma (a standard model of the development of severe oncological disease) was studied.

Figure 13:
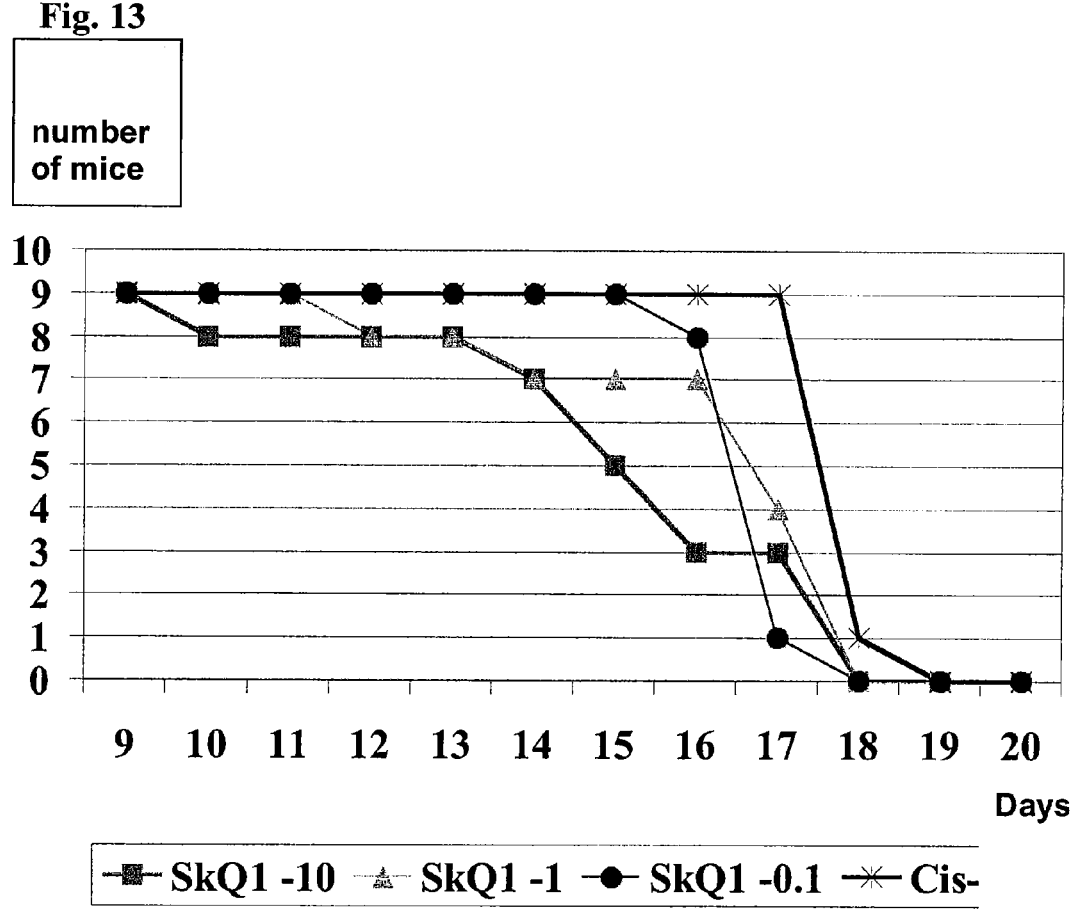
FIG. 13 shows the influence of three different concentrations of SkQ1 on survival rate of mice with acquired Ehrlich ascite carcinoma.

NMRI mice were given a drink containing SkQ1 at 10, 1 or 0.1 µM concentrations. Results (survival rate of mice with acquired Ehrlich ascite carcinoma) are shown in FIG. 13. The negative control for this experiment was pure water, while the positive control was well-known anticancer drug cisplatin.

The results obtained demonstrate anticancer effect of the mitochondrially targeted anticancer drugs corresponding to structure (I).

Experimental Example 14

Photodynamic Effect of the Mitochondrially Targeted Compounds

Compounds corresponding to structure (I) and having photosensitizer activities can induce release of cytochrome c from intermembrane space into cytoplasm and apoptosis.

It was shown that prototype photosensitizers bearing the positive charge (rhodamines, chloromethyl-X-rosamine) accumulated in mitochondria and induce apoptosis in different tumor cells with the moderate photoirradiation. Similar non-mitochondrially targeted compounds cause mainly necrotic cell death after photoirradiation (which may give potential inflammatory complications from photodynamic treatment). The prototype photosensitizers studied to date are not used in practice because of the low quantum yield and maximum absorption in the green section of spectrum. Photosensitizers made on the basis of protoporphyrin and phthalocyanine derivatives and currently used in practice have the high quantum yield, maximum absorption in the red section of spectrum (this improves treatment efficiency of inner tissues) but are accumulated mainly in lysosomes and induce necrosis. Mitochondrial targeting of said molecules incorporated in the compounds of structure (I) would allow the induction of apoptosis of tumor cells with red light photoirradiation of low intensity.

It was shown that compounds bearing the positive charge (rhodamine and phosphonium derivatives) are accumulated and stayed in mitochondria of the fast-growing tumors to a greater extent as compared to the cells of normal tissues. It may be assumed that photosensitizers made on the basis of compounds corresponding to structure (I) must be selectively accumulated in tumors and thus said compounds must be more efficient in photodynamic therapy.

Experimental Example 15

Protective Effect of the Mitochondrial Antioxidant SkQ1 on Fungi Cells of the Yeast *Yarrowia lipolytica* as an Example We showed that mitochondrial antioxidant SkQ1 corresponding to structure (I) partially prevents the death of *Yarrowia lipolytica* cells caused by 10 mM hydrogen peroxide.

Figure 14:
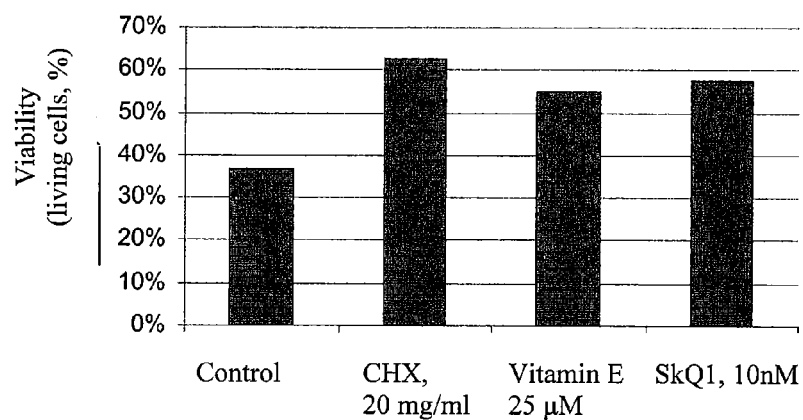
FIG. 14 shows the effect of protein synthesis inhibitor, cycloheximide D (ChD) and antioxidants on cells of *Yarrowia lipolytica* treated with 5 mM hydrogen peroxide. Survival rate was estimated using the number of grown colonies at solid medium. The cells were transferred onto the solid medium after 3 h of incubation.

It can be seen from FIG. 14 that the effects of cycloheximide D, tocopherol and SkQ1 are very similar. The effect of cycloheximide was demonstrated earlier on and is explained by the need of the normal protein synthesis in cells during apoptosis. Concentration of α-tocopherol was 25 μM because this concentration provided the maximum effect on the protection of *Saccharomyces cerevisiae* cells from pheromone- and amiodarone-induced programmed cell death (Pozniakovsky A I, Knorre D A, Markova O V, Hyman A A, Skulachev V P, Severin F F., 2005, J Cell Biol. 168(2):257-69). This concentration was as effective as the 10-fold lower concentration of SkQ1. These results indicate that the mitochondrially targeted antioxidants increase viability of fungi cells and that compounds of SkQ1 type can be used for the protection of industrial producer strains of yeasts, other fungi and microorganisms.

Experimental Example 16

Effect of the Mitochondrial Antioxidant SkQ1 on Development of the Higher Plants Plants cuttings were grown at the artificial agarized medium MS supplemented with 1 μM SkQ1 (3 plants) and with no addition of SkQ1 as a control (3 plants). Cuttings were placed into 50 ml transparent tubes and grown in climate chamber for 3 weeks at 27° C. and periodical illumination (14 h of light, 10 h of darkness). Then the plants were subjected to darkness stress, i.e. were grown in complete darkness for 7 days.

As a result the control plants became colorless while the plants grown in the presence of SkQ1 retained their green color. Then the plants were returned back to the normal lighting conditions and were grown for additional 20 days. After such treatment the plants grown in the presence of SkQ1 became more than 3 times higher in size in comparison to the control plants.

This experimental example demonstrates the positive effect of the mitochondrially targeted antioxidants on a plant as a whole. Consequently such compounds can be used for cultivation of plants on artificial media (the necessary stage in production of genetically modified plants), increase of viability of the cultured plant cells and increase of viability of crops in agriculture.

Those persons skilled in the art will appreciate that the above description is provided by way of example only. However, based on the description above some obvious additions or corrections can be made that allow to obtain all claimed compounds and compositions, useful for the purposes of this invention. Said obvious additions and corrections are within the scope of the invention described below in claims of the invention.

The invention claimed is:

1. A compound having antioxidant activity, which is selected from the group consisting of:

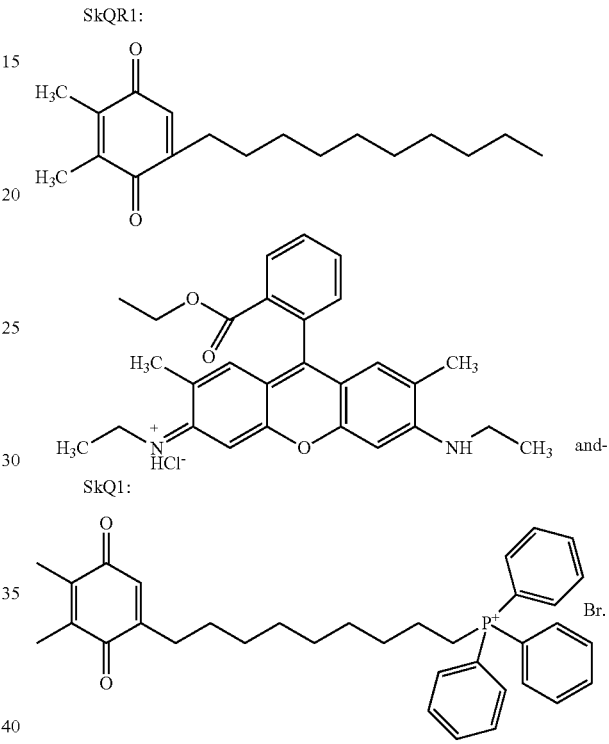

* * * * *